(12) United States Patent
Goto et al.

(10) Patent No.: US 7,684,539 B2
(45) Date of Patent: Mar. 23, 2010

(54) X-RAY TOMOGRAPH

(75) Inventors: Taiga Goto, Kashiwa (JP); Osamu Miyazaki, Moriya (JP); Koichi Hirokawa, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 506 days.

(21) Appl. No.: 10/524,341

(22) PCT Filed: Aug. 28, 2003

(86) PCT No.: PCT/JP03/10971

§ 371 (c)(1),
(2), (4) Date: Feb. 11, 2005

(87) PCT Pub. No.: WO2004/034908

PCT Pub. Date: Apr. 29, 2004

(65) Prior Publication Data

US 2006/0165211 A1     Jul. 27, 2006

(30) Foreign Application Priority Data

Oct. 18, 2002  (JP) ............................. 2002-304463
Mar. 20, 2003  (JP) ............................. 2003-078125

(51) Int. Cl.
*A61B 6/03* (2006.01)
(52) U.S. Cl. ........................... 378/15; 378/4
(58) Field of Classification Search ............ 378/15, 378/4

See application file for complete search history.

(56) References Cited

U.S. PATENT DOCUMENTS 5,047,931 A * 9/1991 Lin .............................. 378/14

5,390,112 A * 2/1995 Tam ............................. 378/17

(Continued)

FOREIGN PATENT DOCUMENTS

JP        8-187240         7/1996

(Continued)

OTHER PUBLICATIONS

Noo et al., Single-slice rebinning method for helical cone-bean CT, 1999, Phys. Med. Biol., vol. 44, pp. 561-570.*
Bruder et al., Single-Slice Rebinning Reconstruction in Spiral Cone-Beam Computed Tomography, IEEE Transactions on Medical Imaging, Sep. 2000, vol. 19, No. 9, pp. 873-887.*

(Continued)

*Primary Examiner*—Edward J Glick
*Assistant Examiner*—John M Corbett
(74) *Attorney, Agent, or Firm*—Cooper & Dunham, LLP

(57) ABSTRACT

A tomograph which determines projection data phase range capable of back projection for each reconfigured voxel with an arbitrary value larger than π so that the absolute values of cone angles at the ends of this phase range is minimized, calculates an approximate straight line for a curve indicating the position of a radiation source with respect to the channel direction position of parallel beam projection data obtained by a parallel beam of a parallel shape viewed from the go-around axis direction generated from the radiation source, and based on the determined projection data range capable of back projection, three-dimension back projects the parallel beam projection data subjected to filter processing created through a filter correction to the back projection region corresponding to the region in concern along the approximate irradiation trace of the radiation beam calculated using the calculated approximate straight line, thereby suppressing generation of the distortion attributed to data discontinuity, simplifying an arcsin calculation and significantly increasing the processing speed of the tomograph.

7 Claims, 20 Drawing Sheets

U.S. PATENT DOCUMENTS

| | | | | |
|---|---|---|---|---|
| 5,796,803 | A * | 8/1998 | Flohr et al. | 378/15 |
| 5,825,842 | A * | 10/1998 | Taguchi | 378/15 |
| 5,889,833 | A * | 3/1999 | Silver | 378/15 |
| 6,097,784 | A * | 8/2000 | Tuy | 378/4 |
| 6,490,333 | B1 * | 12/2002 | Hsieh | 378/4 |
| 6,947,584 | B1 * | 9/2005 | Avila et al. | 382/131 |
| 2003/0073893 | A1 * | 4/2003 | Hsieh | 600/407 |
| 2003/0128801 | A1 * | 7/2003 | Eisenberg et al. | 378/19 |

FOREIGN PATENT DOCUMENTS

| | | |
|---|---|---|
| JP | 10-290798 | 11/1998 |
| JP | 11-4823 | 1/1999 |
| JP | 11-253434 | 9/1999 |
| JP | 2000-225114 | 8/2000 |
| JP | 2002-291732 | 10/2002 |
| JP | 2003-26080 | 1/2003 |

OTHER PUBLICATIONS

Kudo et al., Three-Dimensional Helical-Scan Computed Tomography Using Cone-Beam Projections,1992, Systems and Computers in Japan, vol. 23, No. 12, pp. 75-82.*

Proksa et al., The n-PI-Method for Helical Cone-Bean CT, Sep. 2000, IEEE Transactions on Medical Imaging, vol. 19, No. 9, pp. 848-863.*

Grass et al., Angular weighted hybrid cone-beam CT reconstruction for circular trajectories, 2001, Physics in Medicine and Biology, vol. 46, pp. 1596-1610.*

Suparta, Focusing Computed Tomography, 2000, 15th WCNDT Roma 2000, available at http://www.ndt.net/article/wcndt00/papers/idn142/idn142.htm.*

Turbell, Cone-Beam Reconstruction Using Filtered Backprojection, Feb. 2001, Linkoping Studies in Science and Technology dissertation No. 672.*

Grass et al., 3D cone-beam CT reconstruction for circular trajectories, 2000, Physics in Medicine and Biology, pp. 329-347.*

Suparta, Focusing Computed Tomography, 2000, 15th WCNDT Roma 2000, available at http://www.ndt.net/article/wcndt00/papers/idn143/idn143.htm.*

Wang et al., Half-Scan Cone-Beam X-ray Microtomography Formula, 1993, Scanning, vol. 16, pp. 216-220.*

Tam et al., Backprojection spiral scan region-of-interest cone beam CT, 1999, SPIE, vol. 3661, pp. 433-441.*

Tam et al., Exact cone beam CT with spiral scan, 1998, Physics in Medicine and Biology, pp. 1015-1024.*

* cited by examiner

FIG. 15A
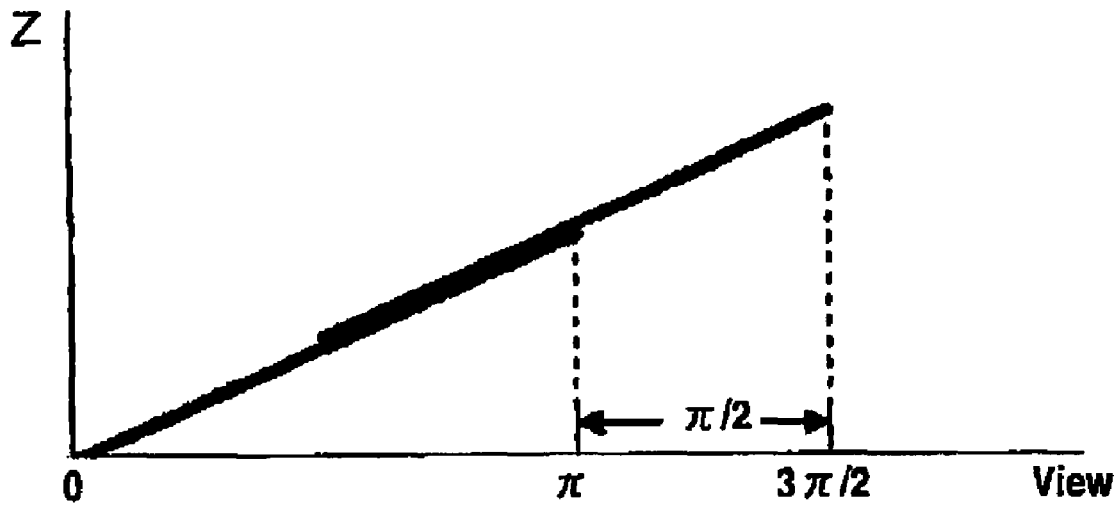
FIG. 15B
FIG. 17
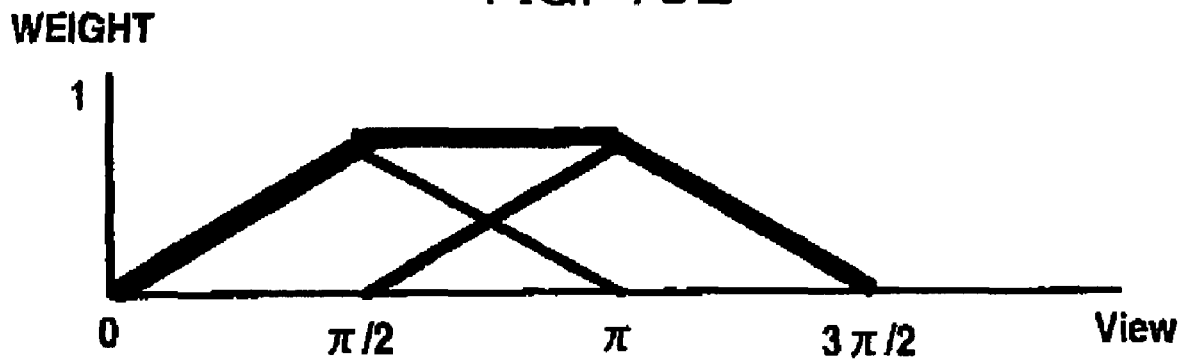
180-DEGREE PHASE RANGE (f=1)
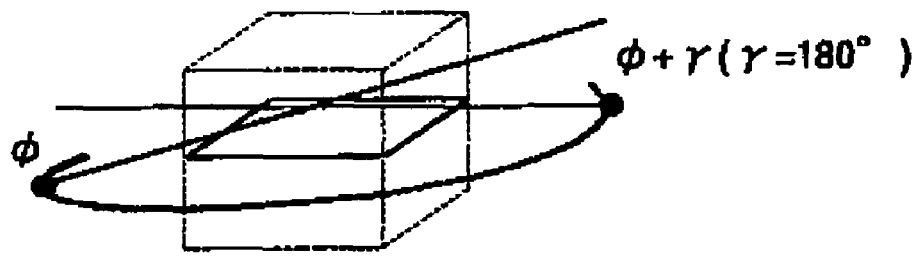

180-DEGREE PHASE RANGE (1 < f < 2)

360-DEGREE PHASE RANGE (f=2)

WEIGHTING FUNCTION (B=$\pi$)

WEIGHTING FUNCTION (B=$3\pi/2$)

WEIGHTING FUNCTION (B=$2\pi$)

X-RAY TOMOGRAPH

TECHNICAL FIELD

The present invention relates to a tomograph which generates a tomographic image of an examinee using projection data obtained from a radiation source moving in the body axis direction relative to the examinee through a radiation detector.

BACKGROUND ART

A conventional three-dimensional back projection method will be explained. A Feldkamp method, Wang method, IHCB method and PI-method proposed as three-dimensional back projection methods are three-dimensional back projection methods which capture a cone beam spreading (having an angle of inclination) in both the slice (body axis) direction and channel (rotation) direction irradiated to multi-row radiation detectors as a collection of a plurality of rows of fan beams spreading only in the channel direction, carry out filter correction processing similar to a two-dimensional back projection method on the fan beam projection data obtained from each detector row or parallel beam projection data obtained by replacing the fan beam by parallel beam through rearrangement processing and carry out back projection processing along the trace of the beam to thereby obtain a reconfigured image.

FIG. 7 shows a reconfigurable condition of a Wang method and FIG. 8 shows a reconfigurable condition of a PI-method. Here, reference character FOV denotes an effective field of view region, SOD denotes a distance between an X-ray tube and the go-around axis of a CT device and SID denotes a distance between the X-ray tube and detector. The Wang method is a method corresponding to a Feldkamp method adapted to image taking of a spiral orbit and has a back projection phase width of $\pi$ to $2\pi$.

An example of a PI-method is disclosed in JP-A-11-253434. This is also a back projection method applicable to image taking of a spiral orbit and is a reconfiguration method for back projecting a $\pi$ range in which the phase varies from one voxel to another to improve a bed moving speed using the Wang method. The PI-method can set the back projection phase range for each voxel to $\pi$ by limiting the vertical direction of an X-ray beam to be back projected using a spiral located opposite to the X-ray focal position.

An example of the IHCB method is disclosed in JP-A-11-4823. This method consists of an algorithm for back projecting a back projection phase range which varies from one voxel to another and the back projection phase width is either $\pi$ or an entire possible data range which varies from one voxel to another.

Next, problems of these conventional technologies will be explained.

The Feldkamp method is an image reconfiguration method for image taking of a circular orbit and is not applicable to image taking of a spiral orbit. The Wang method is an image reconfiguration method for image taking of a spiral orbit and can correct influences of movement of an examinee, which is practiced by the conventional two-dimensional back projection method by extending the back projection phase width beyond $\pi$ (increasing data redundancy), but results in a poor data utilization rate and the pitch (hereinafter referred to as "measuring throughput") of the spiral during image taking needs to be very small. By improving the PI-method and IHCB method so that the back projection phase range according to the Wang method is widened, their respective measuring throughputs can be drastically improved compared to the Wang method, but they are the back projection methods within the $\pi$ range with data redundancy completely eliminated, and therefore data may be discontinuous at the start phase and end phase of the back projection phase range due to influences of movement of the examinee, which is likely to become a strong artifact and appear on the image.

Here, data redundancy will be explained. The data redundancy refers to a breadth of a phase range within which not only phase data but also opposed phase data is acquired. According to a three-dimensional back projection method, data redundancy changes from one voxel to another. For example, as shown in FIG. 22, when back projection is performed from data obtained by rotating the phase of a radiation source by 180 degrees, the contributing data phase range changes from one reconfiguration pixel to another and a pixel a has data having a phase range of 180 degrees or more, while a pixel b can only acquire data of 180 degrees or less. Furthermore, it is also necessary to consider the beam width in the body axis direction and in this way data redundancy changes from one pixel to another in a complicated manner. For this reason, a complicated redundancy correction is required.

One of problems of these conventional three-dimensional reconfigurations is an increase in a calculation time.

Therefore, when an increase in the amount of calculation from a parallel beam two-dimensional back projection method to a parallel beam three-dimensional back projection method is analyzed, the increased calculation causes (1) an increase in the number of times one-dimensional rearrangement processing is performed, (2) an increase in the number of times reconfiguration filter processing is performed and (3) an addition of calculation of detector row addresses during back projection processing. Here, the main processing that occupies the calculation time in the two-dimensional back projection method and three-dimensional back projection method is back projection processing.

The loads of calculation of the distance between the focus and reconfiguration point during the calculation of detector row addresses and arcsin calculation (calculation of the z position of the focus of the parallel beam of the following Expression 1) are particularly large and occupy the major portion of causes of increases in the calculation time.

$$z_S = (J \cdot (\phi + \arcsin(t_f/SOD))/2\pi) + z_{SO} \quad \text{[Expression 1]}$$

See FIG. 29.

Suppose SOD is a distance between a radiation source and a go-around axis, $\phi$ is a phase angle of the parallel beam, J is a relative movement distance from a radiation source to an examinee per rotation of a scanner on a radiation detector 13, $t_f$ is the position in the channel direction, $z_s$ is the position of the radiation source 11 in the z direction and $z_{so}$ is $z_s$ when the go-around phase of the radiation source is 0. Therefore, if these calculations can be simplified, it is possible to significantly increase the processing speed of the tomograph.

It is an object of the present invention to provide a tomograph capable of suppressing generation of the distortion attributed to data discontinuity and obtaining a tomographic image of high image quality not eliminating data redundancy but rather using it in three-dimensional back projection calculations.

It is another object of the present invention to provide a tomograph capable of simplifying arcsin calculation on a fan-parallel beam conversion and back projection processing according to a set FOV range in three-dimensional back projection calculations and significantly increasing the processing speed of the tomograph without degrading image quality.

DISCLOSURE OF THE INVENTION

1. In order to attain the above described objects, the present invention is a tomograph comprising a radiation source and a radiation detector arranged opposite to each other, between which a bed with an examinee placed thereon is provided, the radiation source and radiation detector turning around the bed which can be moved with respect to this go-around axis, radiation irradiated from the radiation source and passing through the examinee being detected using the radiation detector, and reconfiguration means for creating a three-dimensional tomographic image in a region in concern of an object from the detected projection data, wherein the reconfiguration means determines for each voxel a projection data range capable of back projection having an operating projection data phase width of 180 degrees or more, superimposes a reconfiguration filter, assigns weights to data of the same phase or opposite phase for each phase for this projection data range and performs three-dimensional back projection on this filter-processed projection data over the determined data range capable of back projection along the irradiation trace of the radiation beam.

Since the tomograph of the present invention determines the projection data phase range used for each voxel, it is possible to determine the projection data phase range for each voxel so that absolute values of the angles of inclination of radiation beams become the same at both ends of the projection data, thereby use projection data with a small cone angle, provide redundancy using weighting means and correct the data for each voxel using a weighting function, thereby suppressing generation of the distortion attributed to discontinuity in the data phase direction and obtain images of high quality. The tomograph of the present invention requires no redundancy processing which would require complicated calculations, thus making it possible to create images at high speed.

2. The present invention described in the item 1 is characterized in that when determining the above described data range, a projection data range is determined so that the difference in the absolute values of cone angles at both ends of the projection data range used is reduced.

3. The present invention described in the item 2 is characterized in that the projection data phase width used is determined so as to be the same phase width for each voxel.

The tomograph according to the invention described in the items 2 and 3 is characterized in that determining means for determining the projection data phase range used for each voxel determines the projection data range so that the difference in the absolute value of cone angles at both ends of the actually used projection data range becomes small or determines the projection data range so that the projection data phase width used has the same phase width for each voxel, which allows projection data with a small cone angle to be used. Furthermore, by equalizing the absolute values of angles of inclination of radiation beams at both ends of the projection data exactly, it is possible to calculate the position of the detector row direction from the data start direction or end direction simultaneously and further calculate the same phase range at the time of back projection of each reconfigured voxel and thereby determine a weighting function for redundancy corrections using a single expression and perform calculations at high speed.

4. The present invention described in the item 1 is characterized in that the projection data range capable of back projection is either 270 degrees or 360 degrees.

The tomograph of the present invention described in the item 3 uses either 270 degrees or 360 degrees as the projection data range capable of back projection, and assigns weights to data using 270 degrees in the phase direction, and can thereby reduce discontinuity at the data end to a minimum. This 270-degree data corrects a discontinuity at the 180-degree data end using a data phase with smallest discontinuity having a 90-degree phase difference and can reduce data discontinuity to a minimum, and thereby realize reconfiguration of high quality.

5. The invention described in any one of the items 1 to 4 is characterized in that projection data whose number of images taken per rotation is a multiple of the number of sides C of a polygonal display pixel is acquired and the reconfiguration means comprises back projection means for superimposing the reconfiguration filter on this projection data, grouping data at the same channel position and having projection phases in the go-around direction shifting by $N\pi/2$ (N=1, 2, 3, . . . ) [rad] at a time and performing back projection to a square image array group by group.

6. The invention described in any one of the items 1 to 4 is characterized in that the reconfiguration means converts the projection data obtained to data including fan beam data and parallel beam data whose number of images taken per rotation is a multiple of the number of sides C of a polygonal display pixel, superimposes the filter on this projection data, groups data at the same channel position and having projection phases in the go-around direction shifting by $N\pi/2$ (N=1, 2, 3, . . . ) [rad] at a time and performs back projection to a square image array group by group.

The tomograph of the invention described in the items 5 and 6 is a method for enhancing the speed of back projection requiring the maximum calculation time in creating an image. In order to enhance the speed of back projection, the present invention takes advantage that the shape of the reconfigured image array is polygonal and that image taking is performed while circling around the reconfigured image, the invention described in the item 5 takes images with a view which is a multiple of the number of sides of a display pixel, performs fan beam reconfiguration and the invention described in the item 6 converts data to data whose number of views is a multiple of the number of sides of a display pixel through rearrangement processing and performs parallel beam reconfiguration. In all cases, the invention groups projection data whose phase in the go-around direction shifts by $N\pi/2$ (N=1, 2, 3, . . . ) [rad] at a time, back projects the square image group by group, and can thereby reduce the number of times the channel direction position in a full reconfiguration and interpolation coefficient are calculated. This is because when the reconfigured image is square, the data of a phase differing exactly by $N\pi/2$ (N=1, 2, 3, . . . ) [rad] and the square reconfigured image have the same positional relationship. Furthermore, the number of views is set to a multiple of 4 to calculate data of a phase differing by $N\pi/2$ (N=1, 2, 3, . . . )[rad] exactly and it is possible to create images by calculating channel positions within a range of ¼ of a full revolution ($\pi/2$ [rad]) in the cases of both a full reconfiguration and a half reconfiguration. In this way, in the case of a full reconfiguration, the amount of calculation becomes ¼ and though calculations are carried out using one calculator, a calculation result close to a result of a parallel calculation using four calculators can be obtained and it is possible to realize high performance at low cost.

7. The invention described in any one of the items 1 to 6 is characterized in that associating means is provided for associating pixel intervals in the body axis direction of the image using polygonal display pixels with the relative moving speed between the object and the radiation source in the go-around axis direction.

8. Furthermore, the invention described in the item 7 is characterized in that the associating means is constructed so that the relationship between pixel interval rpitch in the body axis direction of the square image and the relative moving speed J in the go-around axis direction of the object and the radiation source is expressed by J=2·N·rpitch (N=1, 2, 3 . . . ).

9. The tomograph according to the invention described in the items 7 and 8 is characterized in that at the phase of Nπ (N=1, 2, 3 . . . ) [rad] of the radiation source, the position on the radiation detector at which the beam passing through a voxel I (x, y, z) whose body axis direction position is Z [mm] and a voxel I (−x, −y, NJ/2+Z) whose body axis direction position is N·J/2+Z[mm] intersects remains the same, and therefore when a beam passing through a voxel is calculated at a certain view at the time of back projecting, this is equivalent to simultaneous calculations of the row positions of phases differing by Nπ (N=1, 2, 3, . . . ) [rad] from each other and when an image is generated from data with a plurality of revolutions obtained by taking images through spiral scanning, it is possible to enhance the speed of back projection which requires a maximum time for image generation.

10. Furthermore, the present invention is a tomograph comprising a radiation source and a radiation detector made up of two-dimensionally arranged detection elements, arranged opposite to each other, between which a bed with an examinee placed thereon is provided, the radiation source and radiation detector turning around the bed which can be moved with respect to this go-around axis, radiation irradiated from the radiation source and passing through the examinee being detected using the radiation detector, and reconfiguration means for creating a three-dimensional tomographic image in a region in concern of the examinee from the detected projection data, wherein the reconfiguration means determines a projection data phase range capable of back projection for each reconfigured voxel, calculates an approximate straight line for a curve indicating the radiation source position with respect to the channel direction position of parallel beam projection data corresponding to the region in concern obtained by a parallel beam of a parallel shape viewed from the go-around axis direction generated from the radiation source, corrects each row of the projection data by multiplying a coefficient which is dependent on the angle of inclination of radiation from the radiation source, carries out one-dimensional rearrangement processing for obtaining parallel beam projection data from the fan beam projection data obtained from a fan-shaped fan beam viewed from the go-around axis direction generated from the radiation source, and superimposes the reconfiguration filter on the parallel projection data to generate filter-processed parallel projection data and three-dimension back projects the parallel beam projection data subjected to the filter processing based on the determined projection data range capable of back projection to the back projection region corresponding to the region in concern along the approximate irradiation trace using the approximate straight line.

The tomograph of the present invention three-dimension back projects the filter-processed parallel beam projection data to the back projection region corresponding to the region in concern based on the projection data range capable of back projection determined by the operating data phase range calculating means along the approximate irradiation trace of the radiation beam calculated using an approximate straight line by the approximate straight line calculating means for calculating an approximate straight line for the curve indicating the radiation source position relative to the channel direction position corresponding to the region in concern of the parallel beam projection data obtained by the parallel beam of a parallel shape viewed from the go-around axis direction generated from the radiation source, and therefore as opposed to the conventional focus position calculation of a parallel beam which includes arcsin calculation and has an increased load, this arcsin calculation is replaced by an approximate straight line, simplifying the amount of calculation in the parallel beam three-dimensional back projection method and thereby significantly increasing the processing speed of the tomograph.

11. The present invention described in the item 10 is characterized in that the reconfiguration means performs redundancy correction weighting for generating a weighting factor from a weighting function in the phase direction to correct data redundancy at each phase according to the phase width of this determined projection data, and the parallel beam three-dimensional back projection means assigns the weighting factor obtained by the redundancy correction weighting means to the projection data within the determined projection data phase range and performs three-dimensional back projection along the approximate trace to the back projection region.

12. The tomograph of the present invention described in the item 11 is characterized in that in determining the projection data phase range, it is possible to determine the phase range of fπ [rad] in the view direction and perform a redundancy correction using the weighting function by the redundancy correction weighting means. Thus, it is possible to provide data with redundancy (extending the back projection phase width beyond 180 degrees), assign weights using the weighting function, reduce discontinuity at the data ends (at the start/end of image taking) and obtain an image with the influence of movement of the examinee reduced to a minimum.

13. Furthermore, the invention described in the item 10 is characterized in that the operating data phase range calculation means determines the projection data range capable of back projection for each reconfigured voxel so that the maximum cone angle of the beam back projected for each voxel becomes narrowest.

The tomograph of the invention described in the item 13 determines the back projection phase range for each voxel by the operating data phase range calculation means so that the maximum cone angle becomes a minimum, and can thereby reduce influences of deterioration of image quality by the cone angle to obtain better image quality and improve the relative moving speed (so-called measuring throughput) between the examinee and focus in the Z direction.

14. Furthermore, the invention described in the item 10 is characterized in that in calculating the operating data phase range calculation, the projection data range capable of back projection for each reconfigured voxel is determined so that the phase direction range of the beam back projected for each voxel is set to the narrowest possible range.

The tomograph of the invention described in the item 14 determines the back projection phase range for each voxel by the operating data phase range calculation means so that the number of views becomes small, and can thereby improve time resolution for each voxel. Furthermore, combining the invention with the redundancy correction weighting means described in the item 13 can obtain better image quality in a region where the examinee moves fast. Furthermore, by setting the back projection phase range for each voxel to the time range in which images are taken at the same time whenever possible so that the time position of the respective voxels in the displayed images come closer to one another, it is possible to shorten the time width contributing to the reconfigured image and improve time resolution.

BRIEF DESCRIPTION OF DRAWINGS

FIG. 15A is a spiral measuring diagram when 270-degree data is used;

FIG. 15B is a characteristic diagram showing a weighting function corresponding to other spiral measurement when 270-degree data is used;

FIG. 17 is a perspective view showing an example of a back projection data phase range when 180-degree phase range (f=1) is used;

BEST MODE FOR CARRYING OUT THE INVENTION

Embodiment 1

With reference now to the attached drawings, embodiments of the present invention will be explained in detail below.

Figure 1:
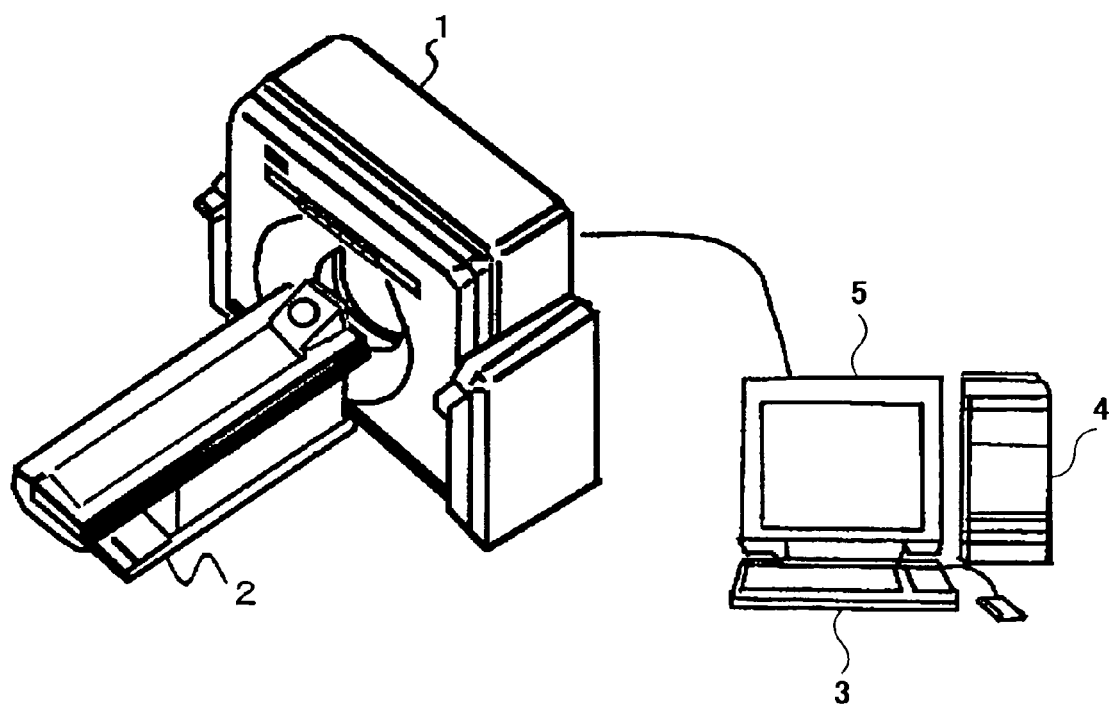
FIG. 1 is a schematic view of a tomograph of the present invention.

FIG. 1 is a schematic outside view of a tomograph according to an embodiment of the present invention. The tomograph comprises a scanner 1 used for image taking, a bed 2 to place and move an examinee, an input device 3 made up of a mouse and keyboard, etc., for inputting measuring reconfiguration parameters such as bed moving speed information and reconfiguration position, a calculation device 4 for processing data obtained from a multi-row detector and a display device 5 which displays a reconfigured image.

Figure 2:
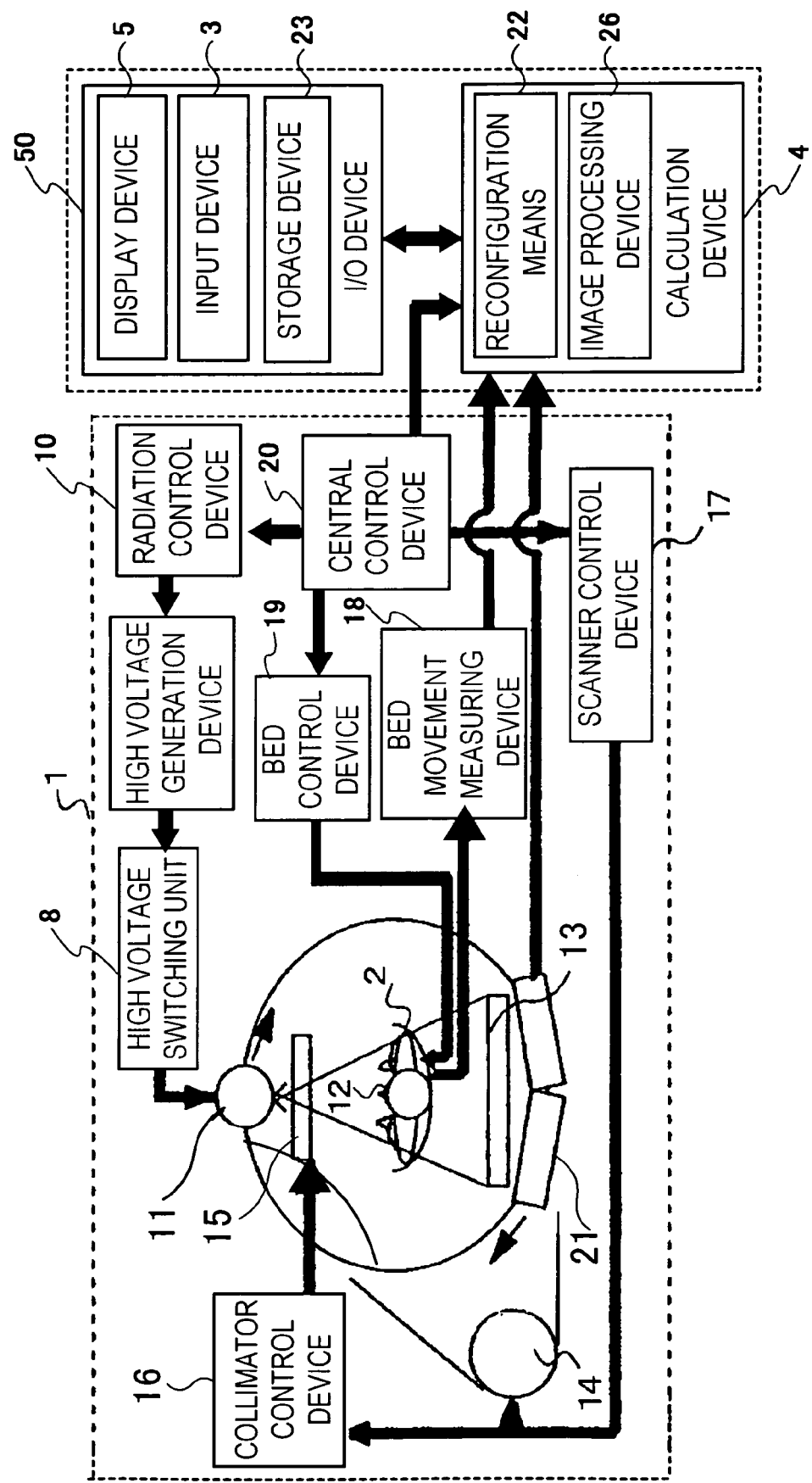
FIG. 2 is a block diagram of the tomograph shown in FIG. 1.

FIG. 2 is a block diagram of the tomograph shown in FIG. 1.

The scanner 1 consists of a bed 2, a high voltage switching unit 8, a high voltage generation device 9, a radiation source 11 such as a radiation generation device having a radiation control device 10, a radiation detector 13 placed opposite to the radiation source 11 with respect to an examinee 12, a go-around drive device 14 which drives this radiation detector 13 and radiation source 11 in the go-around direction and a collimator 15 which controls a radiation region to be irradiated from the radiation source 11, etc. The scanner 1 further consists of a collimator control device 16 which controls the collimator 15, a scanner control device 17 which controls the go-around drive device 14, a bed movement measuring device 19 which measures an amount of relative movement between the bed control device 18 which controls the bed 2 and a central control device 20 which controls these devices.

Image taking conditions (bed moving speed, tube current, tube voltage, slice position, etc.) and reconfiguration parameters (region in concern, reconfigured image size, back projection phase width, reconfiguration filter function, etc.) are input from the input device 3, a control signal necessary for image taking is sent from the central control device 20 to the radiation control device 10, bed control device 18 and scanner control device 17 based on the instruction and upon reception of an image taking start signal, image taking is started. When image taking is started, the radiation control device 10 sends a control signal to the high voltage generation device 9, a high voltage is applied to the radiation source 11, and radiation is irradiated from this radiation source 11 to the object 12. At the same time, a control signal is sent from the scanner control device 17 to the go-around drive device 14, and the radiation source 11, radiation detector 13 and preamplifier 21 turn relative to the object 12. On the other hand, the bed 2 carrying the examinee 12 is stopped by the bed control device 18 during a circular orbit scan or translated in parallel in the go-around axis direction of the radiation source 11, etc., during a spiral orbit scan. The go-around drive device 14, scanner control device 17 and bed control device 18, etc., constitute a drive device which turn the radiation source 11 and radiation detector 13 relative to the examinee 12 and which is relatively movable in the axial direction of the examinee 12.

With the irradiation region restricted by the collimator 15, the radiation irradiated from the radiation source 11 is absorbed and attenuated by each tissue inside the examinee 12, passed through the examinee 12 and detected by the radiation detector 13. The radiation detected by the radiation detector 13 is converted to a current, amplified by the preamplifier 21 and input to the calculation device 4 as a projection data signal. The projection data signal input to the calculation device 4 is processed by the reconfiguration means 22 for reconfiguring the image inside the calculation device 4.

The reconfigured image is saved in a storage device 23 in an I/O device 50 and displayed by an image processing device 26 on the display device 5 as a tomographic image.

Figure 3A:
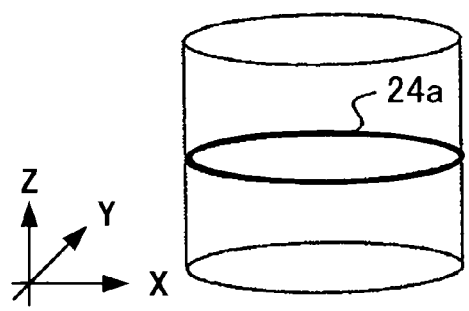
FIGS. 3A and 3B are conceptual diagrams showing a focus trace of a circular orbit scan and spiral orbit scan.
Figure 3B:
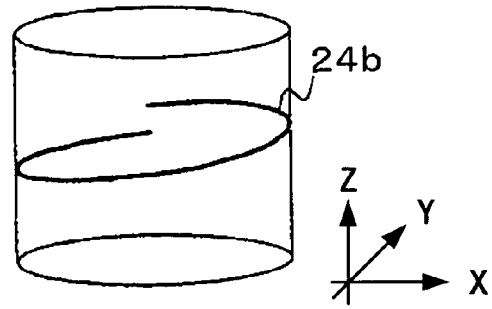

FIGS. 3A and 3B are conceptual diagrams showing focus orbits of a circular orbit scan and spiral orbit scan.

FIG. 3A shows a movement trace 24*a* of the radiation source (focus) during a circular orbit scan and FIG. 3B shows a movement trace 24*b* of the radiation source (focus) during a spiral orbit scan. If the detector is formed of a single row, when images are taken on a circular orbit as in the case of the movement trace 24*a* it is possible to accurately reproduce the images at the positions of the radiation source by carrying out filter correction two-dimensional back projection. However, when images are taken on a spiral orbit as in the case of the movement trace 24*b*, carrying out filter correction two-dimensional back projection alone results in streak-shaped artifact at that position due to data discontinuity at the end position of image taking. Thus, by applying data interpolation to the data obtained on the spiral orbit as in the case of the movement trace 24*b*, the data is corrected to the circular orbit data like the movement trace 24*a* and then filter correction two-dimensional back projection is carried out. In this way, it is possible to obtain an image with reduced discontinuity. The degree of artifact in this case is determined by the degree of discontinuity in the X-ray source trace, that is, the degree of artifact changes depending on the moving speed of the examinee. For example, in a single row type spiral scanning X-ray tomograph (SDCT), the spiral pitch (ratio of the moving speed of the examinee to the thickness of the X-ray beam in the go-around axis direction) is generally used to an extent that substantially the entire image taking region can be covered with the data on the opposite side taken into consideration.

Figure 4A:
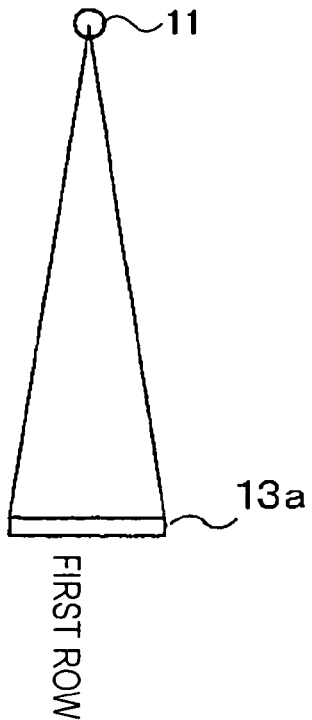
FIGS. 4A and 4B are side views of the waist part of a single radiation detector and multi-row radiation detector.
Figure 4B:
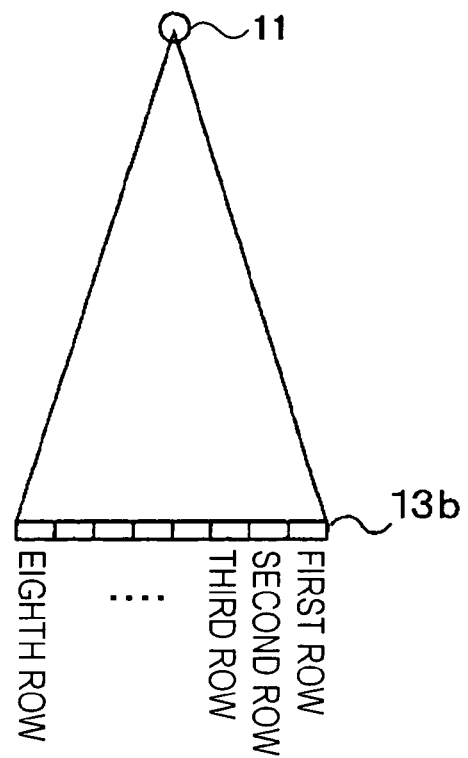

FIGS. 4A and 4B are schematic side views of the single row radiation detector 13*a* and multi-row radiation detector 13*b*.

In FIG. 4B, a plurality of multi-row radiation detectors 13*b* whose width per row is narrower than that of the single row radiation detector 13*a* in FIG. 4A are arranged in a plurality of rows in the go-around axis direction, realizing a wider detector than the single row radiation detector 13*a* as a whole.

Figure 5A:
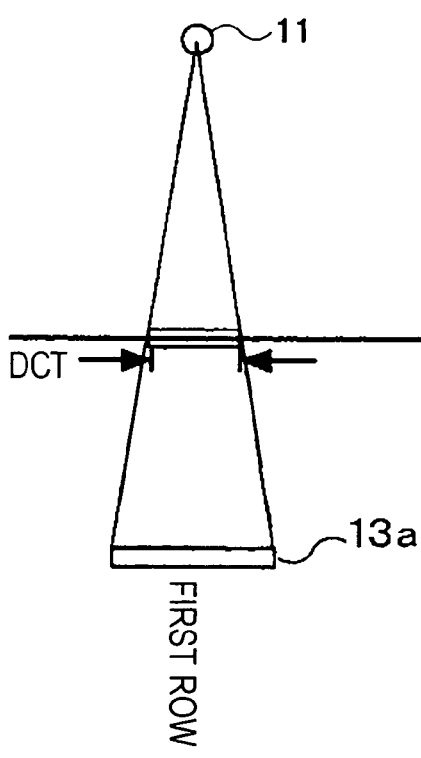
FIGS. 5A and 5B illustrate a collimation thickness of an X-ray beam per row of the single radiation detector and multi-row radiation detector.
Figure 5B:
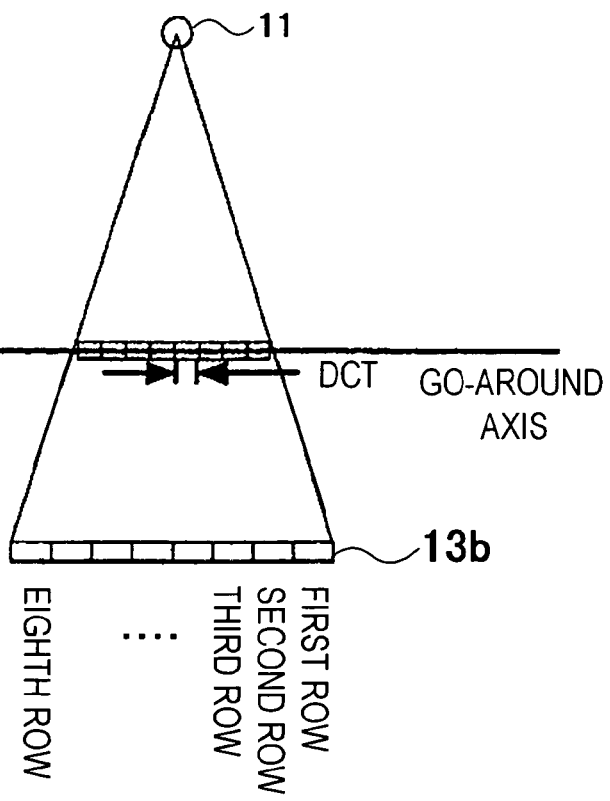

FIGS. 5A and 5B are schematic side views illustrating a thickness in the go-around axis direction (hereinafter, referred to as a "detector collimation thickness DCT") of the radiation beam per one row of detectors at the position of the collimator 15 in the case of using the single row radiation detector 13*a* and the multi-row radiation detector 13*b*, respectively.

In the case of the multi-row radiation detector 13*b* shown in FIG. 5B, the detector collimation thickness DCT is smaller than that of the single row radiation detector 13*a* shown in FIG. 5A, but images over a wider range can be taken at a time as a whole. The spatial resolution (body axis resolution) in the go-around axis direction of the tomographic image obtained improves as the detector collimation thickness becomes smaller.

Next, the processing of creating a three-dimensional tomographic image of the object 12 by the reconfiguration means 22 from the projection data detected by the radiation source detector 13 will be explained.

Figure 6:
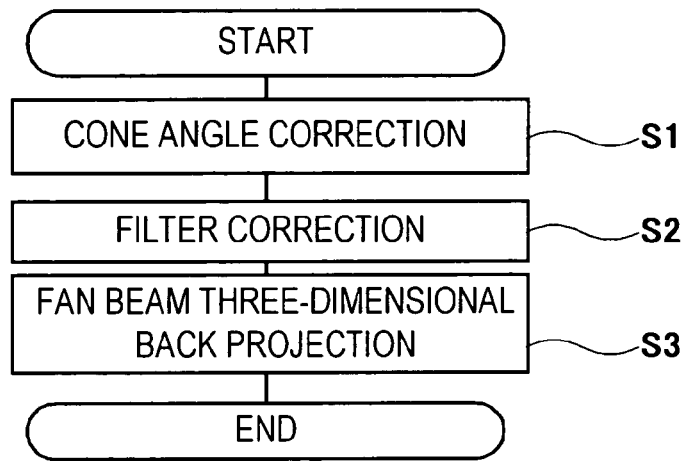
FIG. 6 is a flow chart showing a processing operation by general reconfiguration means.
Figure 7:
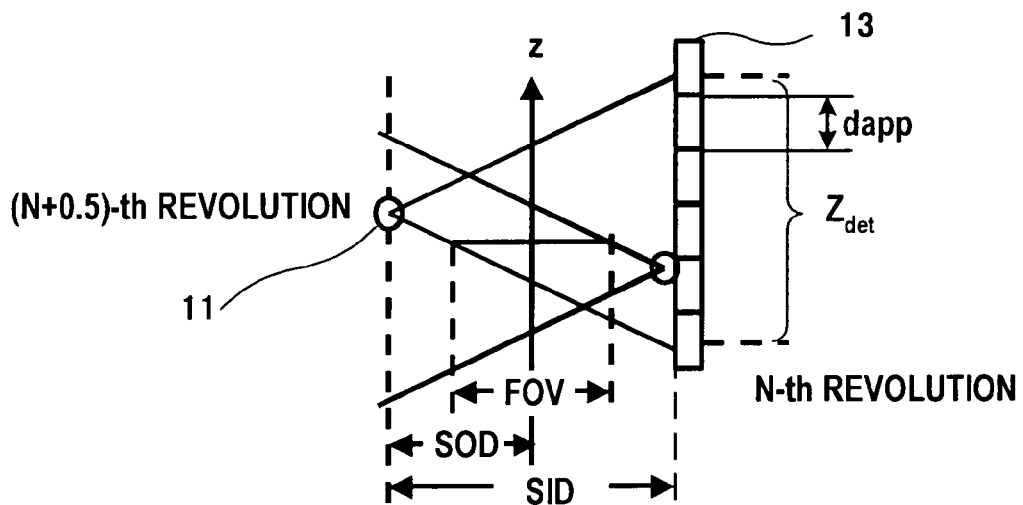
FIG. 7 is a plan view showing a positional relationship between the radiation detector 13 and beam as a reconfigurable condition according to a Wang method.
Figure 8:
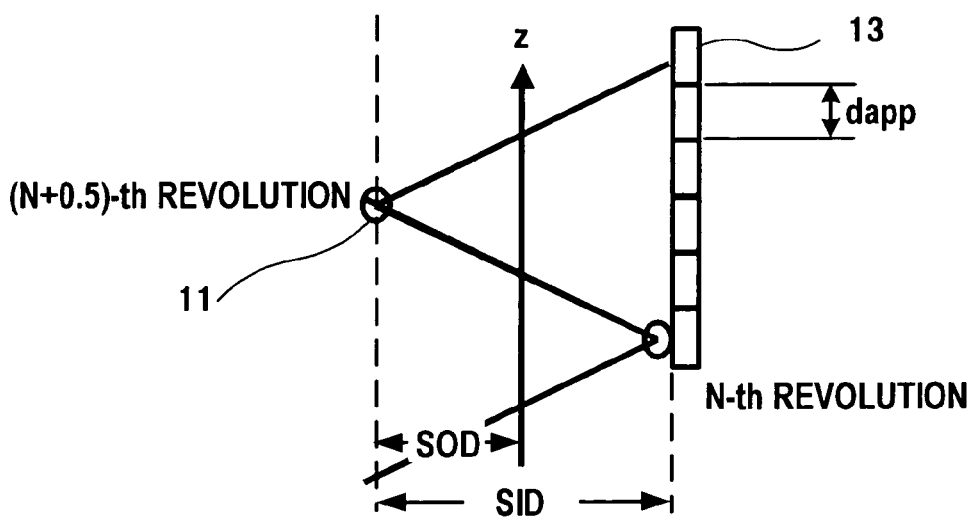
FIG. 8 is a plan view showing a positional relationship between the radiation detector 13 and beam as a reconfigurable condition according to a PI-method.

FIG. 6 is an example of flow chart showing the processing according to the Feldkamp reconfiguration method.

Figure 9:
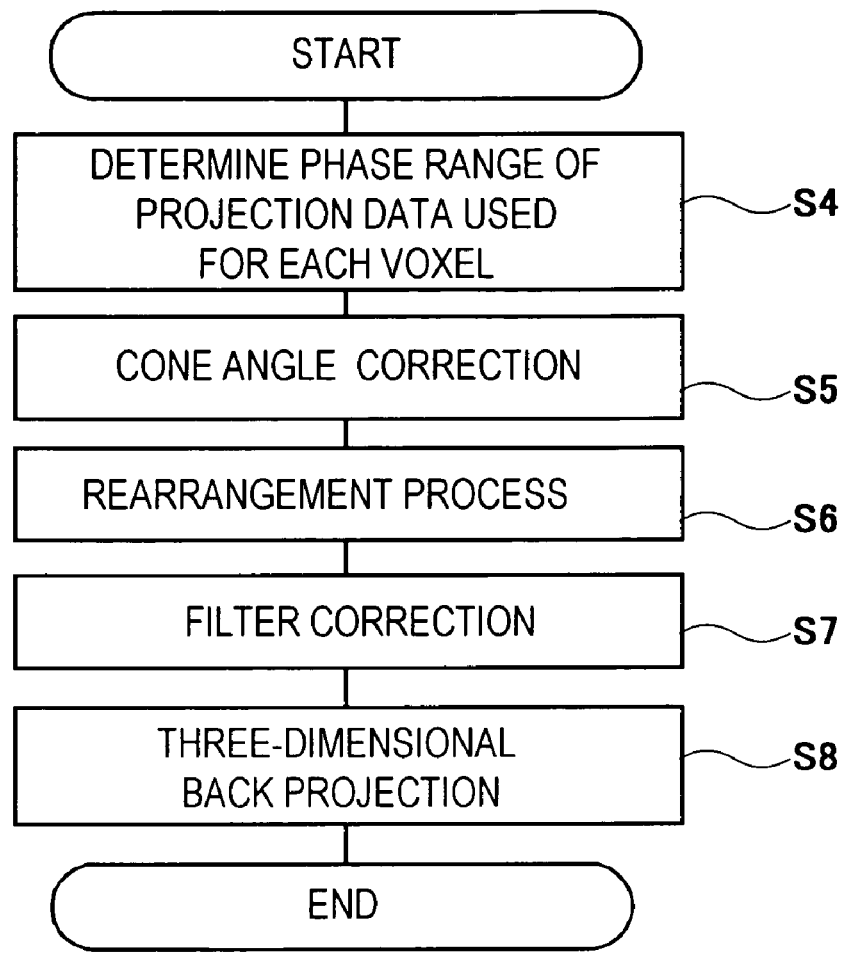
FIG. 9 is a flow chart showing a processing operation of an embodiment of the reconfiguration means of the present invention.

On the other hand, FIG. 9 is a flow chart showing a processing operation of the reconfiguration means 22 of the tomograph according to an embodiment of the present invention. This flow chart assumes processing carried out slice by slice.

The reconfiguration means 22 in FIG. 2 is provided with operating data phase range calculation means for determining a projection data phase range capable of back projecting for each reconfigured voxel, cone angle correction means for multiplying each row of projection data by a coefficient which is dependent on the angle of inclination of radiation from the radiation source, one-dimensional rearrangement processing means for obtaining parallel beam projection data from fan beam projection data obtained from a fan-shaped fan beam viewed from the go-around axis direction generated from the radiation source, filter correction means for superimposing the reconfiguration filter on the parallel beam projection data and creating filter-processed parallel beam projection data and parallel beam three-dimensional back projection means for carrying out three-dimensional back projection on the filter-processed parallel beam projection data to the back projection region corresponding to a region in concern based on the determined projection data range capable of back projection.

Based on the above described configuration, in FIG. 9, the operating data phase range calculation means determines the data range used for each voxel in step S4 first. Next, in step S5, the cone angle correction means multiplies each row of the projection data by a coefficient which is dependent on the angle of inclination of radiation and in step S6, the one-dimensional rearrangement processing means associates the fan beam projection data obtained from a fan-shaped fan beam viewed in the go-around axis direction generated from the radiation source with the parallel beam projection data. Then, in step S7, the filter correction means superimposes the reconfiguration filter on the parallel beam projection data and generates filter-processed parallel beam projection data. Next, in step S8, the parallel beam three-dimensional back projection means performs three-dimensional back projection on the filter-processed parallel beam projection data to the back projection region corresponding to the region in concern based on the determined projection data range capable of back projection.

Next, the respective steps shown in FIG. 9 will be explained.

First, in step S4, the operating data phase range calculation means determines each data range used for each of all voxels in the slice.

Figure 28A:
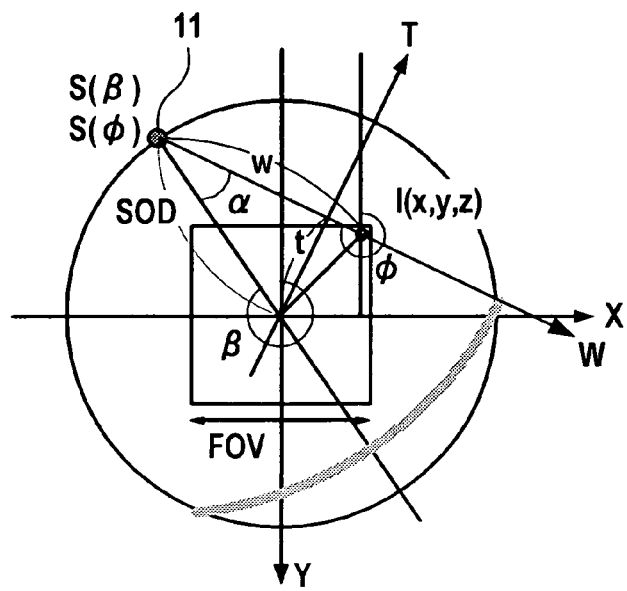
FIGS. 28A, 28B and 28C show a relationship between the figure illustrating calculation processing of the approximate straight line shown in FIG. 27, cone angle, X-ray source and reconfiguration.
Figure 28B:
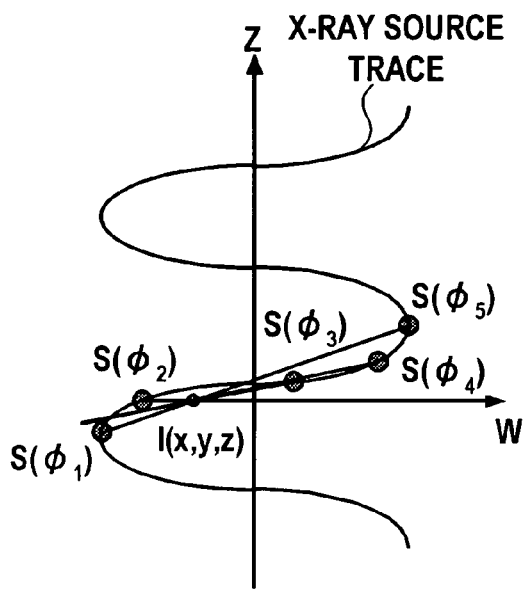
Figure 29:
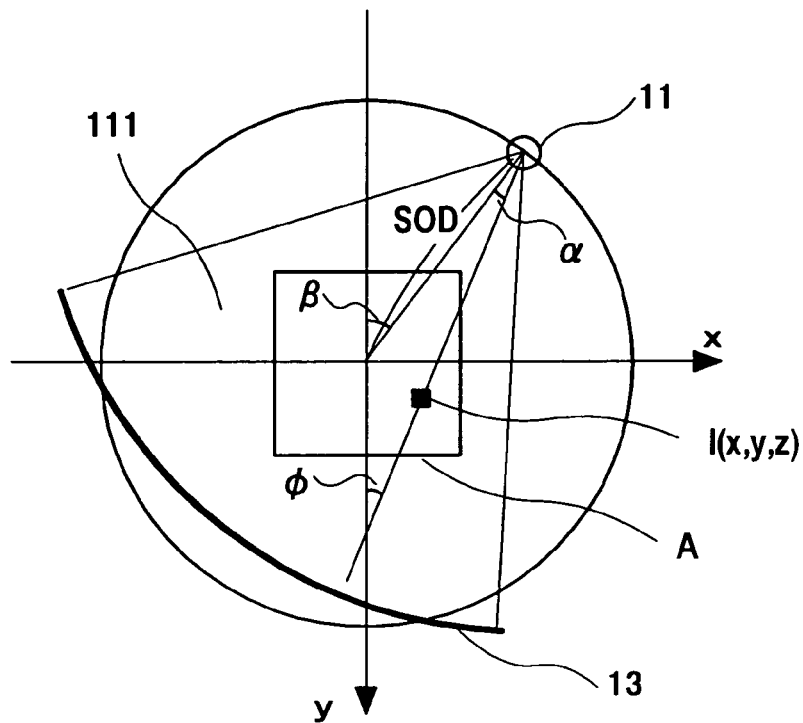
FIG. 29 illustrates determining processing of the projection data phase range.

In the geometry shown in FIGS. 28A, 28B and FIG. 29, suppose the distance between the radiation source 11 and rotation center is SOD, the relative movement distance in the body axis direction of the radiation source 11 with respect to the examinee per rotation of the scanner on the radiation detector 13 (e.g., amount of feeding of the table) is J, the go-around phase of the fan beam source is β, beam spreading angle between the beam directed to the reconfigured voxel I (x, y, z) and central beam is α and the go-around phase of the parallel beam is φ. Then, the fan beam source position $S(\beta) = S(x_S, y_S, z_S)$ is expressed by the following Expression 2. Furthermore, when this is rearranged and replaced by a parallel beam, the fan beam source position is expressed by Expression 3.

$$S(\beta) = S(SOD \cdot \sin\beta, -SOD \cdot \cos\beta, J\beta/2\pi) \quad \text{[Expression 2]}$$

$$S(\phi) = S(SOD \cdot \sin(\phi+\alpha), -SOD \cdot \cos(\phi+\alpha), J(\phi+\alpha)/2\pi) \quad \text{[Expression 3]}$$

Here, suppose the traveling direction of the parallel beam is W, the direction perpendicular to this traveling direction W (channel direction of parallel beam) is T. Then, the T coordinate and W coordinate when the parallel beam at phase φ passes through coordinate (x, y) are expressed by Expression 4 and Expression 5 respectively.

$$T(x,y,\phi) = x \cdot \cos\phi + y \cdot \sin\phi \quad \text{[Expression 4]}$$

$$W(x,y,\phi) = -x \cdot \sin\phi + y \cdot \cos\phi \quad \text{[Expression 5]}$$

Furthermore, the distance s_tz_dist between the X-ray source and T-Z plane (plane passing through the go-around axis and perpendicular to the parallel beam) is expressed by the following Expression 6.

$$s\_tz\_dist(x,y,\phi) = (SOD^2 - T(x,y,\phi)^2)^{1/2} \quad \text{[Expression 6]}$$

Furthermore, when the parallel beam with phase φ passes through the reconfigured voxel I (x, y, z) and crosses the radiation detector 13 whose distance from the radiation source 11 is SID, suppose the coordinates of a system formed of the V axis (the same go-around axis direction as the z axis, the origin position thereof is detector center) of the radiation detector 13 and the X-Y axis are H (x, y, φ). Then, the coordinates are expressed by Expression 7. Here, while the Z axis matches the V axis, they are different in that the Z axis uses the scan start position as the origin position and the V axis uses the detector center as the origin position.

$$H(x,y,\phi) = (z - J(\phi+\alpha)/2\pi) \cdot SID/(s\_tz\_dist(x,y,\phi) + W(x,y,\phi)) \quad \text{[Expression 7]}$$

Here, in FIG. 28A, α=arcsin(t/SOD)=A't+B', A' and B' are coefficients of approximate straight lines obtained by approximating arcsin(t/SOD).

Figure 10:
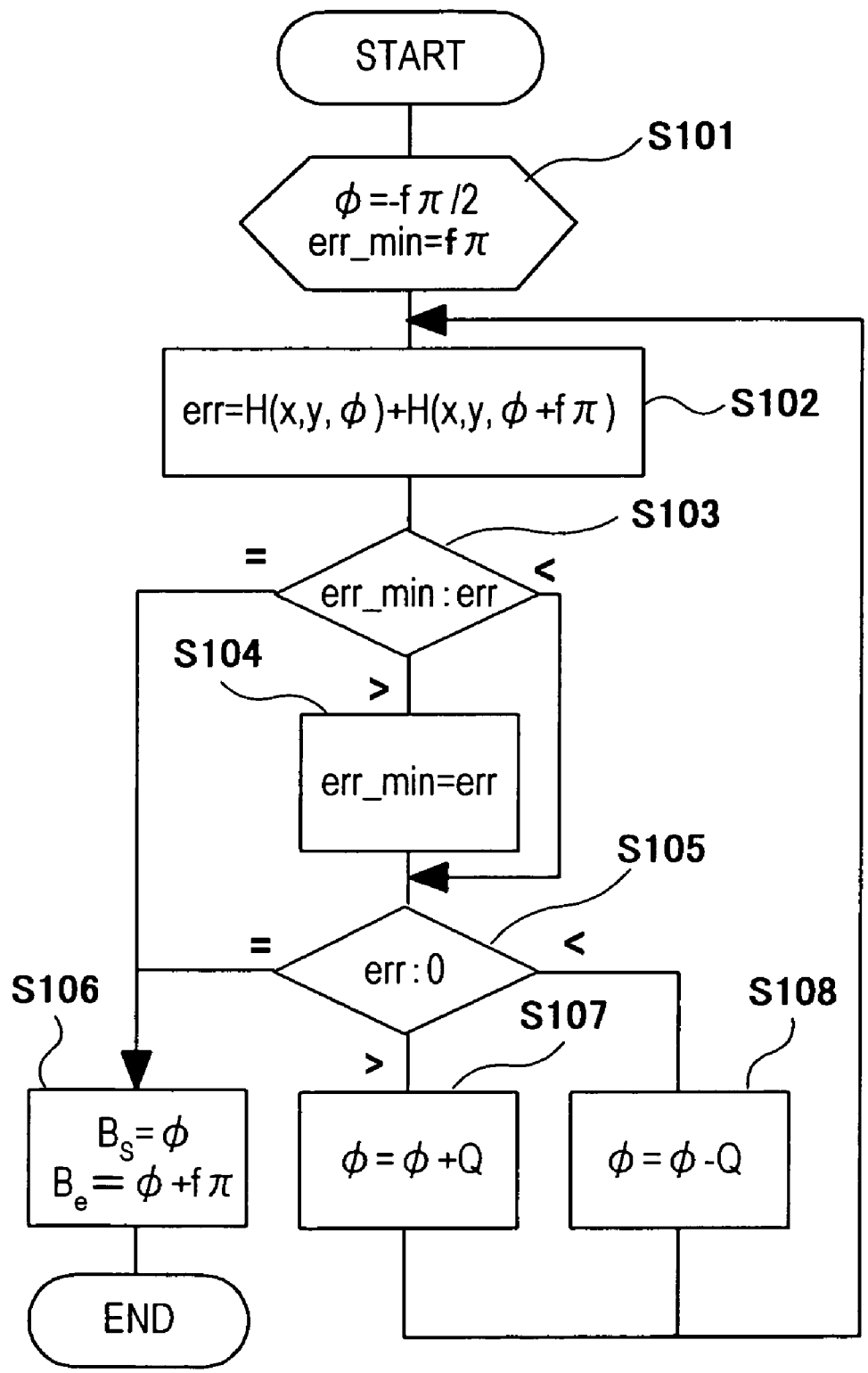
FIG. 10 is a flow chart showing an operation of the operating data position range determining processing shown in FIG. 9.
Figure 28C:
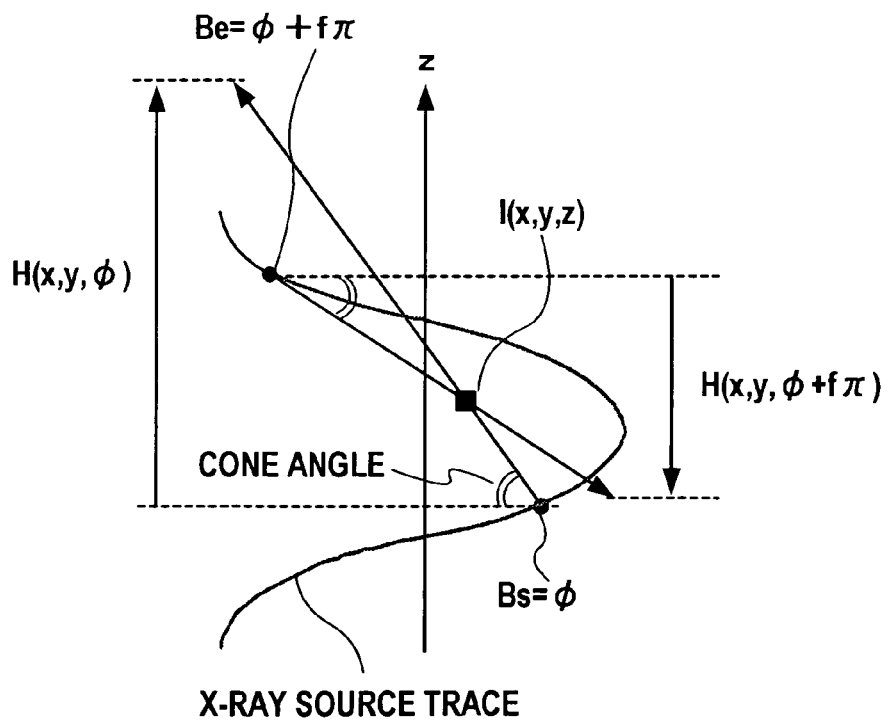

Based on FIG. 28C, how the phase range calculated in step S4 is determined will be explained. As already described, this phase range differs from one voxel to another, and therefore the phase range is determined for each voxel and expressed by f here. The phase range is determined by selecting one which narrows the plane spreading angle of the cone beam with respect to the vertical line in the detector direction, that is, cone angle most. f is normally between 1 and 2. At $B_s$ and $B_e$ which are the ends of phase range fπ used to back project the reconfigured voxel I (x, y, z), in order to minimize the absolute value of the cone angle, it is possible to select a go-around phase φ of the parallel beam so that the difference in the absolute values between the coordinates H(x, y, φ+fπ) (corresponds to finally determined cone angle) and coordinates H(x, y, φ) (corresponds to initial cone angle) become the smallest possible value. More specifically, an example of calculation algorithm of the data range with the smallest cone angle is shown in FIG. 10. As shown in step S101, when it is assumed that the initial value of φ is −fπ/2, calculation phase accuracy is Q (phase angle per view is normally used as Q, but when priority is given to the processing time, a phase angle exceeding one view can also be used), the sum of the H(x, y, φ+fπ) and H(x, y, φ) is err(x, y, φ) (hereinafter expressed as "err") and a minimum value of this sum err is err_min (initial value is err_min=fπ), err is expressed by Expression 8 and Expression 9 shown in step S102.

$$err = H(x,y,\phi) + H(x,y,\phi+f\pi) \quad \text{[Expression 8]}$$

$$\text{if [err\_min>err], err\_min=err} \quad \text{[Expression 9]}$$

Here, when φ increases, err decreases and when φ decreases, err increases, and so the following Expression 10 and Expression 11 are repeated.

$$\text{if [err>0]}, \phi=\phi+Q \quad \text{[Expression 10]}$$

$$\text{if [err<0]}, \phi=\phi-Q \quad \text{[Expression 11]}$$

Through this repeating processing, if err is compared with err_min as shown in step S103, when err becomes a minimum value, minimum values appear repeatedly and err=err_min, and so by carrying out repeating processing until err=err_min is obtained, it is possible to select φ as shown in step S104 so that the difference in the absolute values between coordinates H(x, y, φ+fπ) and coordinates H(x, y, φ) becomes the smallest possible value as shown in step S105. If the decision in step S105 results in err>0, φ=φ+Q as in step S107, and if err<0, φ=φ−Q as in step S108. Thus, the phase range (Bs≦φ<Be) is expressed by the following Expression 12 and Expression 13.

$$Bs(x,y,z) = \phi \quad \text{[Expression 12]}$$

$$Be(x,y,z) = \phi + f\pi \quad \text{[Expression 13]}$$

Here, the phase range has been determined using the simplest method as described above, but this is the problem of calculation of a minimum value of the function err (φ) in the phase range (−fπ/2≦φ<fπ/2) and it is also possible to use an existing method, for example, Brent's method and golden division method (golden section search) and combine various methods to calculate φ and φ+fπ so that err(φ) becomes a minimum value. Furthermore, it is also possible to increase the processing speed by optimizing the initial value when φ=−fπ/2 is determined.

Furthermore, with regard to the phase range fπ used to back project the reconfigured voxel (x, y, z), it is also possible to determine Bs and Be by determining go-around phase φ of the parallel beam so that the absolute value of the angle of inclination of the beam (cone angle) of the X-ray beam becomes small at the end of the phase rangeπ and extend the data range to both ends of the data range as shown the following Expression 14 and Expression 15.

$$Bs(x,y,z) = \phi - (f-1)\pi/2 \quad \text{[Expression 14]}$$

$$Be(x,y,z) = \phi + f\pi + (f-1)\pi/2 \quad \text{[Expression 15]}$$

Next, the cone angle correction step of multiplying each row of the parallel beam projection data by a coefficient which is dependent on the cone angle using the cone angle correction means in step S5 shown in FIG. 9 will be explained.

Filter correction in reconfiguration is filtering corresponding to the distance from the go-around axis in the reconfigured image and it is necessary to apply a filter corresponding to the cone angle to correct the influences of beam inclination. Here, suppose data before filter correction is $P_{para}(\phi, t, v)$, data after filter correction is $fP_{para}(\phi, t, v)$, and the reconfiguration filter function is $g(t)$. Then, the reconfiguration filter processing can be expressed as shown in Expression 16 using a convolution method and of this, the cone angle correction is the portion expressed by Expression 17. As is evident from Expression 16, since the cone angle correction term is a coefficient corresponding to the detector row position v (cone angle), cone angle correction can be carried out both before and after filter correction. For this cone angle correction, a publicly known technology in the three-dimensional back projection techniques including a Feldkamp method is applicable.

$$fP_{para}(\phi, t, v) = \int_{-\infty}^{\infty} \frac{SID}{\sqrt{SID^2 + v^2}} P_{para}(\phi, t-t', v) g(t') dt' \qquad \text{[Expression 16]}$$

where t' is a variable of integration in Expression 16.

$$SID/\sqrt{SID^2 + v^2} \qquad \text{[Expression 17]}$$

Figure 32A:
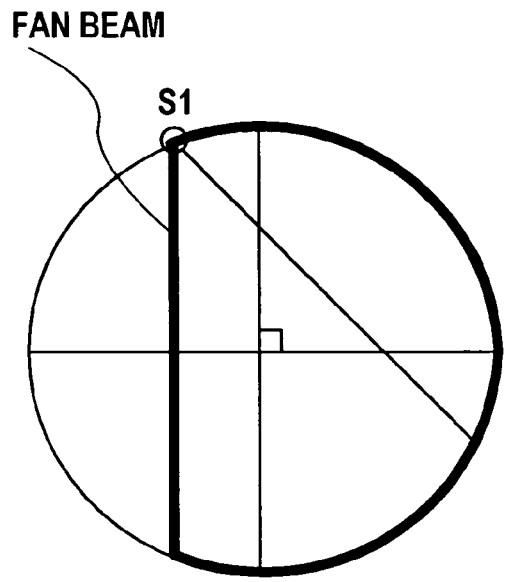
FIG. 32A to FIG. 32D show a relationship between a fan beam and parallel beam.
Figure 32B:
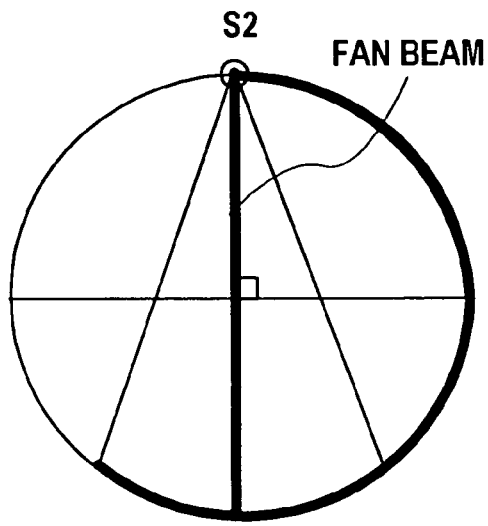
Figure 32C:
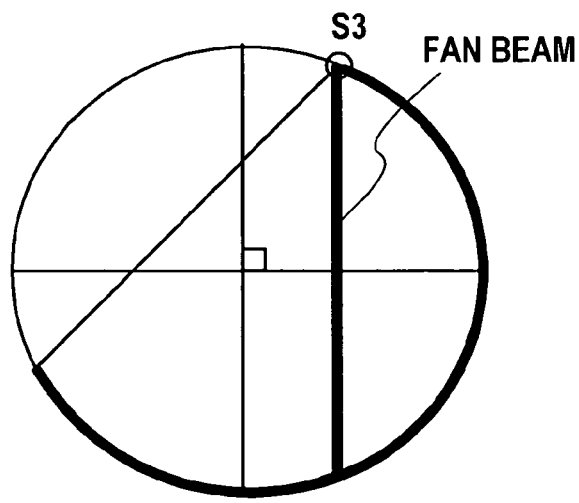
Figure 32D:
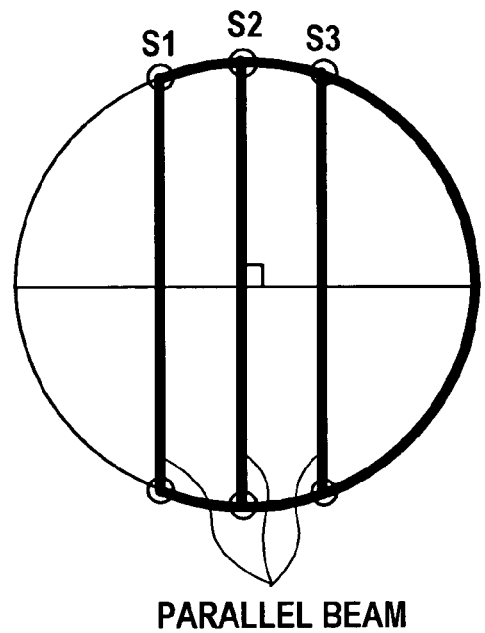

Next, the rearrangement processing (rebinning) using the one-dimensional rearrangement processing means in step S6 shown in FIG. 9 will be explained. Here, FIG. 32A and FIG. 32B show a relationship between a fan beam and a parallel beam. FIGS. 32A to 32C show a 180° reconfiguration of a fan beam and FIG. 32D shows a 180° reconfiguration of a parallel beam. When X-ray beams (S1 to S3) irradiated in the same vector direction viewed from the go-around axis direction are gathered together, it is possible to virtually create a parallel beam as shown in FIG. 32D.

Figure 11A:
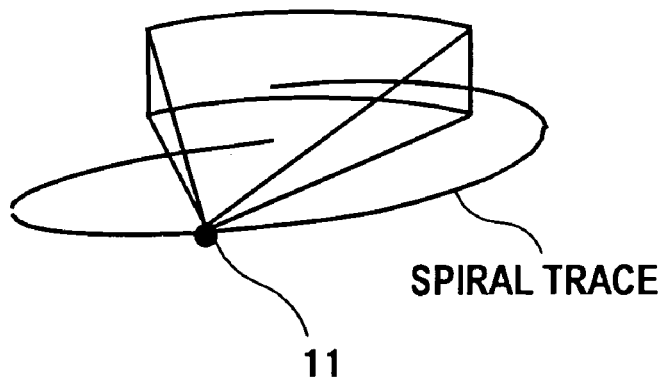
FIGS. 11A and 11B are a perspective view and an exploded view showing spiral traces of the radiation source and radiation detector.
Figure 11B:
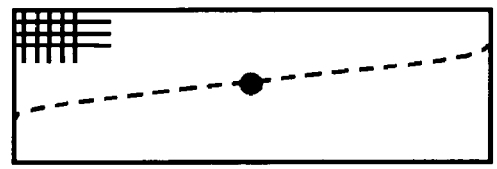
Figure 12A:
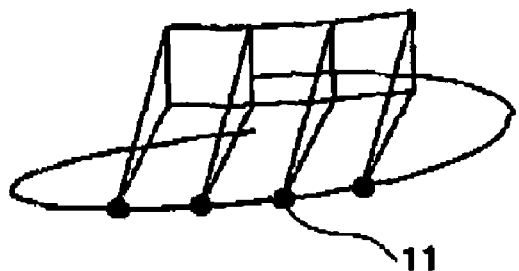
FIGS. 12A and 12B are a perspective view and an exploded view illustrating the operation of the rearrangement processing shown in FIG. 9.
Figure 12B:
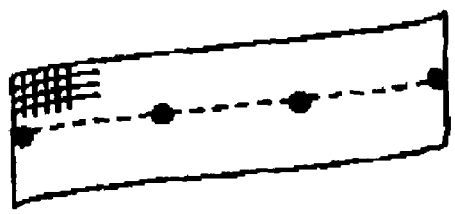

In order to enhance the calculation speed, one-dimensional rearrangement processing is carried out which rearranges a fan beam irradiated in a fan shape viewed from the go-around axis direction as shown in FIG. 11A and FIG. 11B into parallel beams which are parallel viewed from the go-around axis as shown in FIG. 12A (FIG. 12B is an exploded view of FIG. 12A) and FIG. 12B. Furthermore, FIGS. 13A and 13B show the parallel beams rearranged in the go-around axis direction, which will be described later.

Figure 13A:
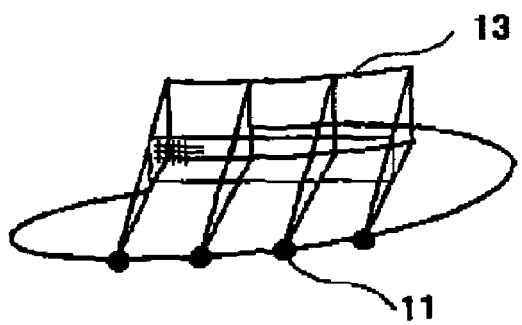
FIGS. 13A and 13B are a perspective view and an exploded view illustrating other rearrangement processing.
Figure 13B:
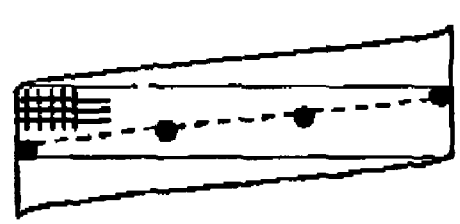

FIGS. 11B, 12B and 13B are exploded views of beams and their respective focuses on the detector corresponding to FIGS. 11A, 12A and 13A. If the fan beam is represented by $P_{fan}(\beta, \alpha, v)$ and parallel beam is represented by $P_{para}(\phi, t, v)$, the fan beam spreading angle in the go-around direction $\alpha = \arcsin(t/SOD)$ and $\beta = \phi + \alpha$ (see FIG. 28A), and therefore the rearrangement processing can be expressed by Expression 18.

$$P_{para}(\phi, t, v) = P_{fan}(\phi + \alpha, \alpha, v)$$

Next, a convolutional calculation (filter correction processing) of a reconfiguration filter carried out to correct blurs of projection data using the filter correction means in step S7 shown in FIG. 9 will be explained.

For filter correction, two types of methods; a convolution method which carries out a convolutional calculation in a real space and a Fourier method which carries out a multiplication in a Fourier space. The convolution method in the former is convolutional processing on a filter function which has been inverse Fourier transformed in a real space. The Fourier method in the latter is processing consisting of transforming into a Fourier space using a Fourier transform, multiplying it by a filter function (spatial frequency filter) and then applying an inverse Fourier transform.

Both are processes mathematically equivalent, but filter processing in a Fourier space which provides high-speed calculation is generally used. For the filter used for reconfiguration, it is possible to select and use Shepp and Logan, Ramachandran and Lakshminarayanan or these filter functions which have been modified through clinical experiences based on clinical experiences. Suppose the parallel projection data is $P_{para}(\phi, t, v)$, the parallel projection data after filter processing is $fP_{para}(\phi, t, v)$ and the reconfiguration filter is $G(\omega)$. Then, Fourier space filtering according to a Fourier method can be expressed by Expression 19.

$$fP_{para}(\phi, t, v) = \qquad \text{[Expression 19]}$$
$$\frac{1}{4\pi^2} \int_{-\infty}^{\infty} \int_{-\infty}^{\infty} (\phi, t, v) \cdot \exp(-i\omega t) dt \cdot G(\omega) \cdot \exp(i\omega t) d\omega$$

On the other hand, when an inverse Fourier transform g(t) of $G(\omega)$ is expressed as shown in Expression 20, the real space filtering according to the convolution method can be expressed by Expression 21.

$$g(t) = \frac{1}{2\pi} \int_{-\infty}^{\infty} G(\omega) \cdot \exp(i\omega t) d\omega \qquad \text{[Expression 20]}$$

$$fP_{para}(\phi, t, v) = \int_{-\infty}^{\infty} (\phi, t-t', v) g(t') dt' \qquad \text{[Expression 21]}$$

where t' is a variable of integration in Expression 21.

For simplicity, the direction in which the filter is applied is assumed to be the T direction here, but it is possible to apply the filter in a high-dimensional direction combining the V direction, T direction and $\phi$ direction. Furthermore, the projection data is handled as continuous data here, but since the projection data is actually discrete data, it is necessary to use a publicly known interpolation method to calculate the projection data in a discrete manner. This discrete calculation method has been practiced so far and is similar to filter correction, etc., used for weighting spiral correction reconfiguration.

Further, implementation of the three-dimensional back projection corresponding to the data range determined by the aforementioned determining means in step S8 of FIG. 9 will be explained.

As shown in FIGS. 28A and 28B, if the reconfigured voxel is I(x, y, z), the V axis direction position that matches the go-around axis on a cylindrical detector centered on the radiation source 11 is v and the position on the T axis substantially orthogonal to this V axis is t, then the reconfigured voxel I(x, y, z) is expressed by Expression 22.

$$I(x, y, z) = \frac{1}{\pi} \int_{Bs(x,y,z)}^{Be(x,y,z)} fP_{para}(\phi, t, v) d\phi \qquad \text{[Expression 22]}$$

where $t = x\cos\phi + y\sin\phi$

-continued $$v = \left(z - \frac{J}{2\pi}(\phi + \alpha)\right)\frac{SID}{SOD\cos\alpha - x\sin\phi + y\cos\phi} + \frac{T}{2\pi}\alpha$$

This algorithm handles the projection data and reconfigured image which should originally be handled discretely as continuous data, and therefore it is actually desirable to use an interpolation method such as Lagrange interpolation and calculate discretely through interpolation in three directions of the phase direction, detector row direction and detector channel direction. To realize a high-speed calculation at the sacrifice of accuracy, the above described v can also be v=(z−Jϕ/2π)·SID/(SODcos α−x sin ϕ+y cos ϕ).

According to such a filter correction three-dimensional back projection method, it is possible to obtain an image of good quality with fewer errors compared to the conventional two-dimensional reconfiguration (weighting spiral correction method). Furthermore, by performing back projection from data with minimum errors (data with a small cone angle) for each voxel to achieve higher image quality and including determining means for determining the data phase range used for each voxel to realize this, or more specifically, determining the data phase range for each voxel so that the absolute values of the angles of inclination of radiation beams become the same at both ends of the data in the phase range, it is possible to use projection data with a smaller cone angle and by performing corrections using a weighting function for each voxel while maintaining redundancy, it is possible to obtain an image with discontinuity in the data phase direction reduced.

Figure 14A:
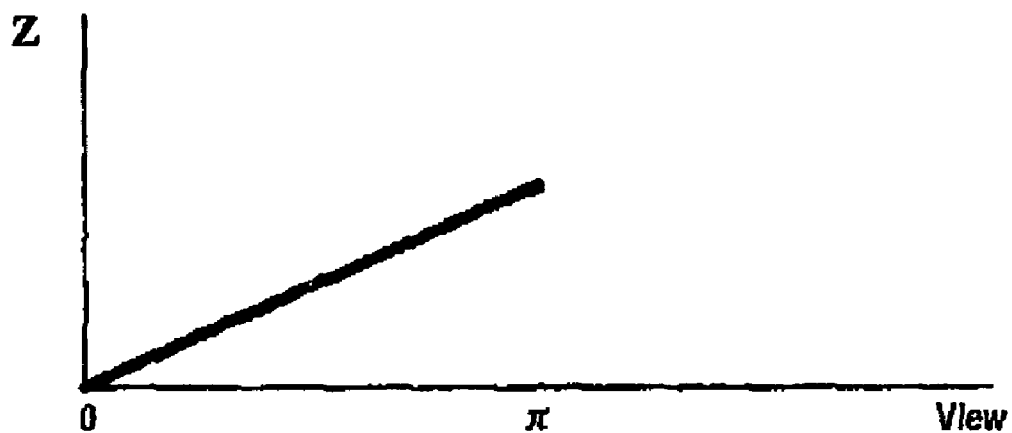
FIG. 14A is a spiral measuring diagram when 180-degree data is used.
Figure 14B:
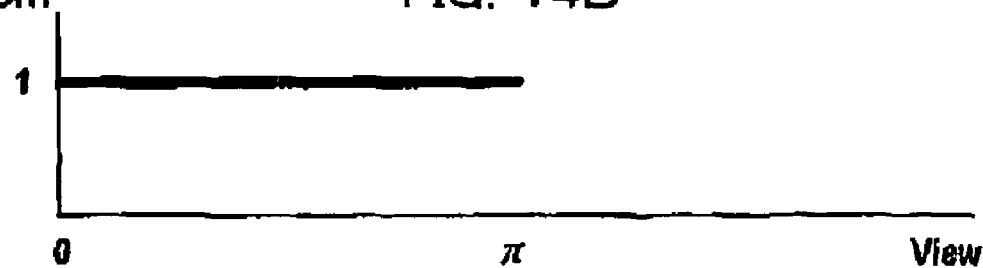
FIG. 14B is a characteristic diagram showing a weighting function corresponding to spiral measurement when 180-degree data is used.
Figure 20A:
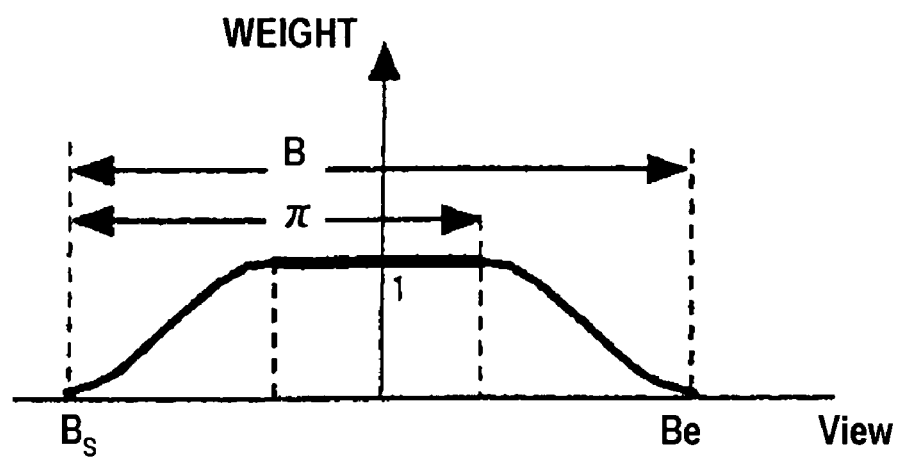
FIGS. 20A and 20B are characteristic diagrams of a weighting function illustrating the redundancy weighting processing shown in FIG. 16.

Especially, by using data 270 degrees in the phase direction and performing weighting as shown in FIG. 20A, it is possible to reduce discontinuity at the ends of data to a minimum. With this 270-degree data, it is possible to correct the discontinuity at 180-degree data ends as shown in FIGS. 14A and 14B using the data phase with the least discontinuity with a phase difference of 90 degrees as shown in FIGS. 15A and 15B. Data becomes discontinuous at the position π in FIGS. 14A and 14B, which may cause artifact. That is, it is possible to reduce the data discontinuity to a minimum and realize reconfiguration of higher quality. Further, if it is possible to accurately equalize absolute values of the angle of inclination of the radiation beam (cone angle) at both ends of data, it is also possible to calculate the detector row direction position from the data start direction and end direction simultaneously and realize a high-speed calculation. Furthermore, since the same phase range is used during back projection of each reconfigured voxel, a weighting function for redundancy correction is determined by a single expression, which allows a high-speed calculation. Errors are mutually corrected at positions of π/2, π in FIG. 15B.

Embodiment 2

Figure 16:
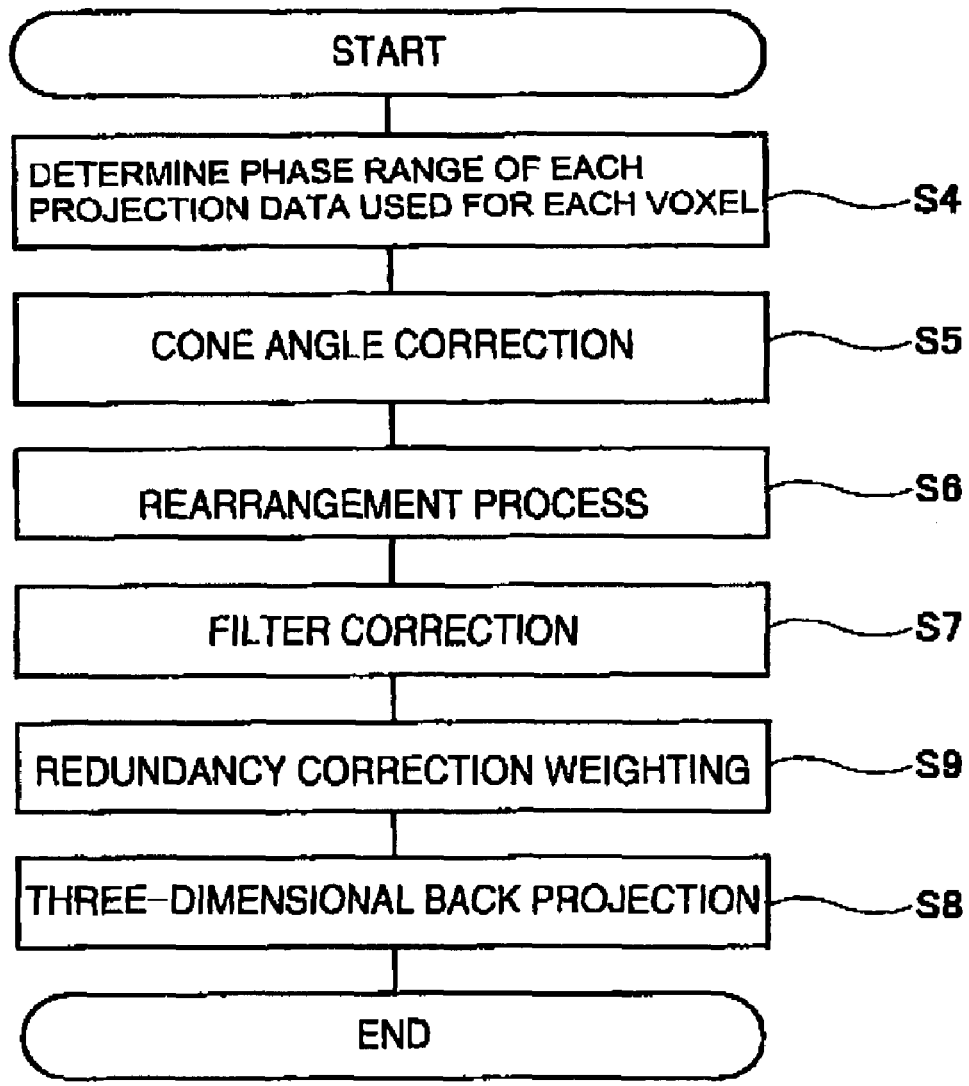
FIG. 16 is a flow chart showing a processing operation of another embodiment of the reconfiguration means of the present invention.

FIG. 16 is a flow chart showing a processing operation of the reconfiguration means 22 according to another embodiment of the present invention.

In this embodiment, a filter correction is performed in step S7 shown in FIG. 9, and then redundancy correction weighting is performed in step S9 and three-dimensional back projection is performed in step S8.

In the case of this embodiment, the reconfiguration means further includes redundancy correction weighting means for realizing a redundancy correction using a weighting function whose shape changes according to the phase width with respect to filter-processed projection data over a projection data range fπ determined and obtained by the operating data phase range means.

Processes in steps S4 to S8 are the same as the procedure already explained using FIG. 9 and therefore a weighting process using the redundancy correction weighting means in step S9 will be explained here.

Figure 18:
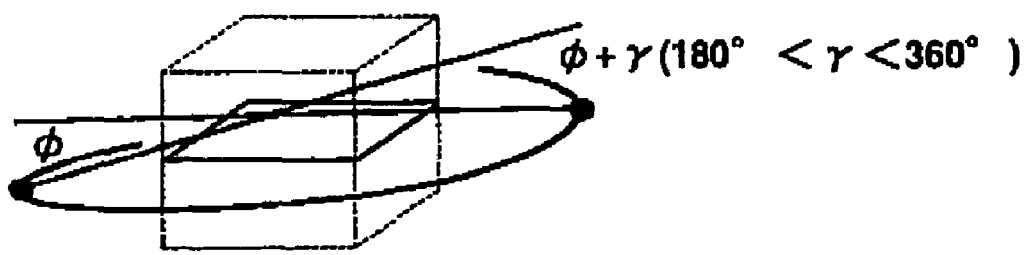
FIG. 18 is a perspective view showing an example of a back projection data phase range when a phase range (1<f<2) from 180 degrees to 360 degrees is used.
Figure 19:
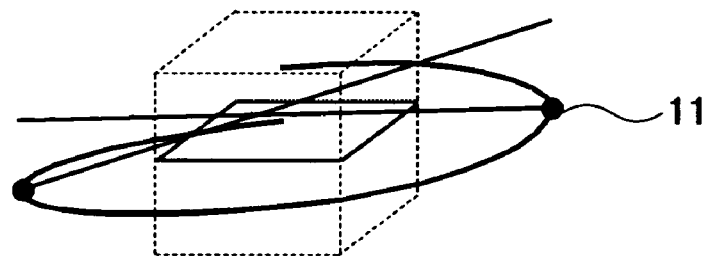
FIG. 19 is a perspective view showing an example of back projection data phase range when 360-degree phase range (f=2) is used.
Figure 21A:
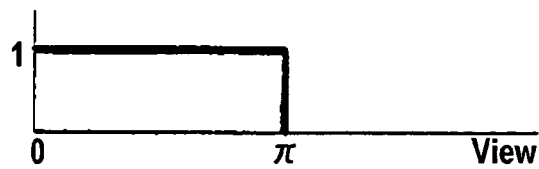
FIGS. 21A to 21C are characteristic diagrams of a weighting function for each phase illustrating redundancy weighting processing shown in FIG. 16.
Figure 21B:
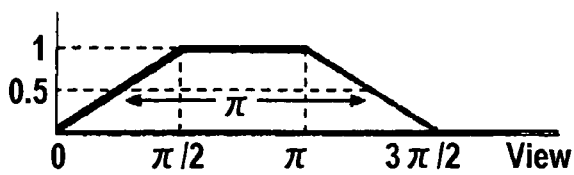
Figure 21C:
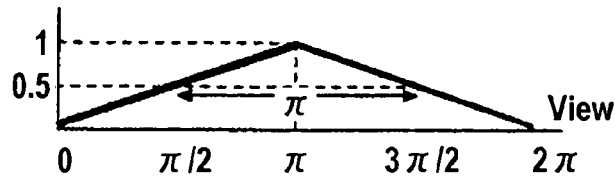

As shown in FIGS. 17 to 19, data of 180 degrees or more is used for each voxel to reconfigure an image and data correction is performed through weighting using the weighting function as shown in FIG. 20A to correct data redundancy. More specifically, as shown in the weighting function W(θ) in FIGS. 21A and 21B and Expression 23 to Expression 25, weighting is performed on the phase data range which varies from one voxel to another so that the sum of weights at the same phase and opposite phase used for back projection remains equal at the respective phases. Here, when the data width used for each voxel is B=fπ, when B=π (when f=1), weighting becomes as shown in FIG. 21A, likewise when B=3π/2 (when f=3/2), weighting becomes as shown in FIG. 21B and when B=2π (when f=2), weighting becomes as shown in FIG. 21C.

$$W(\theta)=((B/2)+\theta)/B-\pi \qquad \text{[Expression 23]}$$

where $[-\pi/2<\theta\leq(2\pi-B)/2]$.

$$W(\theta)=1 \qquad \text{[Expression 24]}$$

where $[-(2\pi-B)/2<\theta\leq(2\pi B)/2]$.

$$W(\theta)=((B/2)-\theta)/B-\pi \qquad \text{[Expression 25]}$$

where $[(2\pi-B)/2<\theta\leq B/2]$.

Figure 20B:
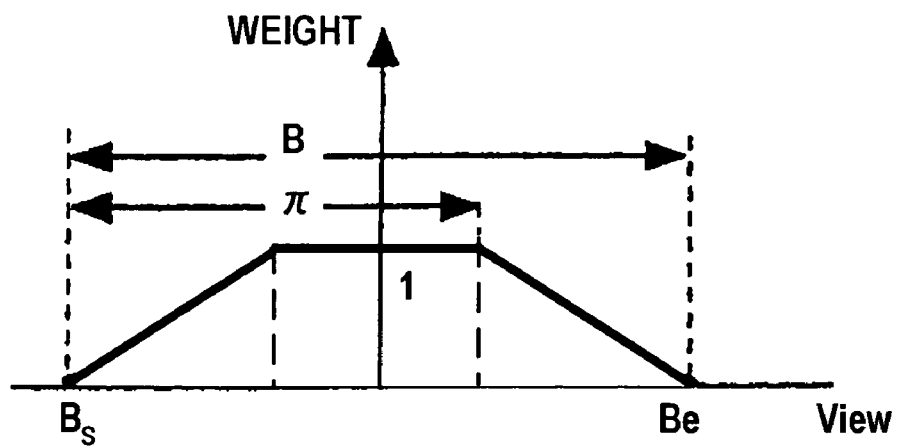

In FIG. 20A and FIGS. 21A to 21C, weighting which linearly changes in the view direction is performed, but it is also possible to perform weighting which changes nonlinearly in the view direction as shown in FIG. 20B. The nonlinear weighting function W'(θ) shown in FIG. 20B can be calculated, for example, from the above described weighting function W(θ) as shown in Expression 26 to Expression 28. Furthermore, only the case with B≦2π is described here, but the case with B>2π can also be easily calculated based on a similar concept.

$$W'(\theta)=3(W(\theta))^2-2(W(\theta))^3 \qquad \text{[Expression 26]}$$

where $[-\pi/2<\theta\leq(2-B)/2]$.

$$W'(\theta)=1 \qquad \text{[Expression 27]}$$

where $[-(2-B)/2<\theta\leq/(2\pi-B)/2]$.

$$W'(\theta)=-3(W(\theta))^2+2(W(\theta))^3 \qquad \text{[Expression 28]}$$

where $[(2\pi-B)/2<\theta\leq B/2]$.

In the above described phase range calculation process for each voxel, such a tomograph is a three-dimensional reconfiguration method which determines a phase range of fπ [rad] in the view direction and carries out a redundancy correction using a weighting function, and provides data with redundancy (extends the back projection phase width beyond 180 degrees), assigns weights using the weighting function, and can thereby reduce discontinuity at the data ends (at the start/end of image taking) and obtain an image with the influence of movement of the examinee reduced to a minimum.

Figure 22:
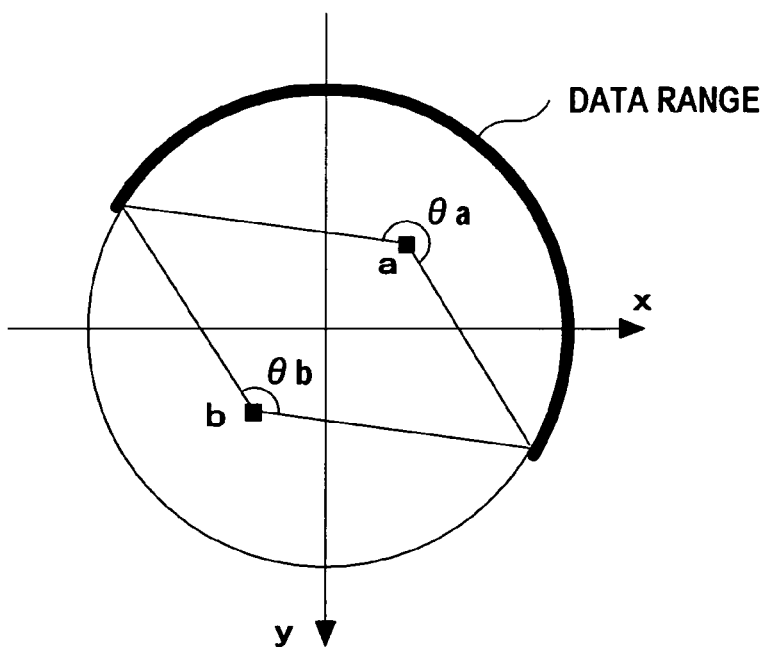
FIG. 22 is a plan view showing a phase range capable of back projection.

When a fan beam reconfiguration is used in a Wang method or IHCB method of the conventional examples, the redundancy (projection phase range) of projection data obtained varies from one voxel to another. For example, when the radiation source performs back projection from data obtained by rotating the phase by 180 degrees as shown in FIG. 22, the data phase range capable of back projection varies from one reconfiguration pixel to another and data in a phase range of 180 degrees or more is obtained at pixel a, but only data of 180 degrees or less is obtained at pixel b. Thus, because data redundancy varies from one pixel to another, when back projection is performed from projection data of 360 degrees or less, complicated redundancy correction processing is required at the time of back projection. In a three-dimensional reconfiguration in particular, a cone angle needs to be considered, and therefore more complicated redundancy correction processing is required, which constitutes one of causes of an increase in the calculation time. Furthermore, this redundancy correction processing is also associated with measuring throughput (relative moving speed between the focus and examinee). Unlike these conventional examples, the present application rather takes advantage of redundancy, uses data with a phase range of 180 degrees or more for each voxel and thereby prevents generation of discontinuity due to movement, etc., and also improves the data efficiency.

Embodiment 3

Figure 23:
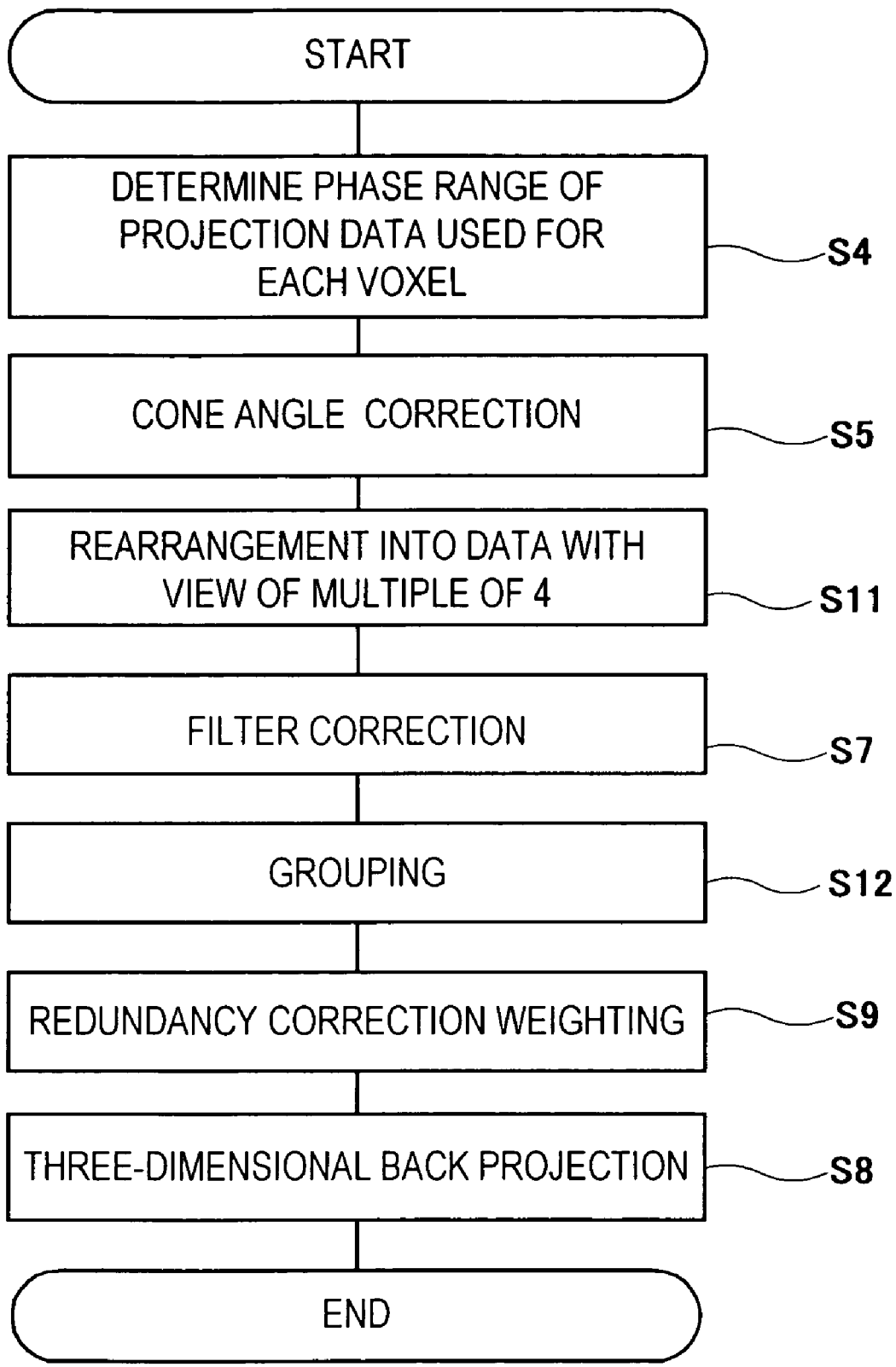
FIG. 23 is a flow chart showing a processing operation of another embodiment of the reconfiguration means of the present invention.

FIG. 23 is a flow chart showing a processing operation of reconfiguration means 22 according to a further embodiment of the present invention.

As shown in FIG. 23, after processes in step S4 and step S5, this embodiment carries out a rearrangement process on projection data of an image taken with a view of a multiple of 4 in step S11. Then, in step S7, a filter correction is performed and in step S12, projection data whose phase in the go-around direction differs by $N\pi/2$ (N=1, 2, 3, ... ) [rad] is grouped by grouping means and in step S9, a redundancy correction weighting process is carried out and in step S8, the grouped projection data is back projected to a square image group by group.

In order to realize such processing, means for acquiring projection data whose number of images taken per rotation is a multiple of 4 is provided, the reconfiguration means 22 includes means for superimposing a filter on this projection data, grouping means for grouping data at the same channel position and whose projection phase in the go-around direction differs by $N\pi/2$ (N=1, 2, 3, ... ) [rad] and back projection means for back projecting into a square image array group by group using this grouping means.

Figure 24:
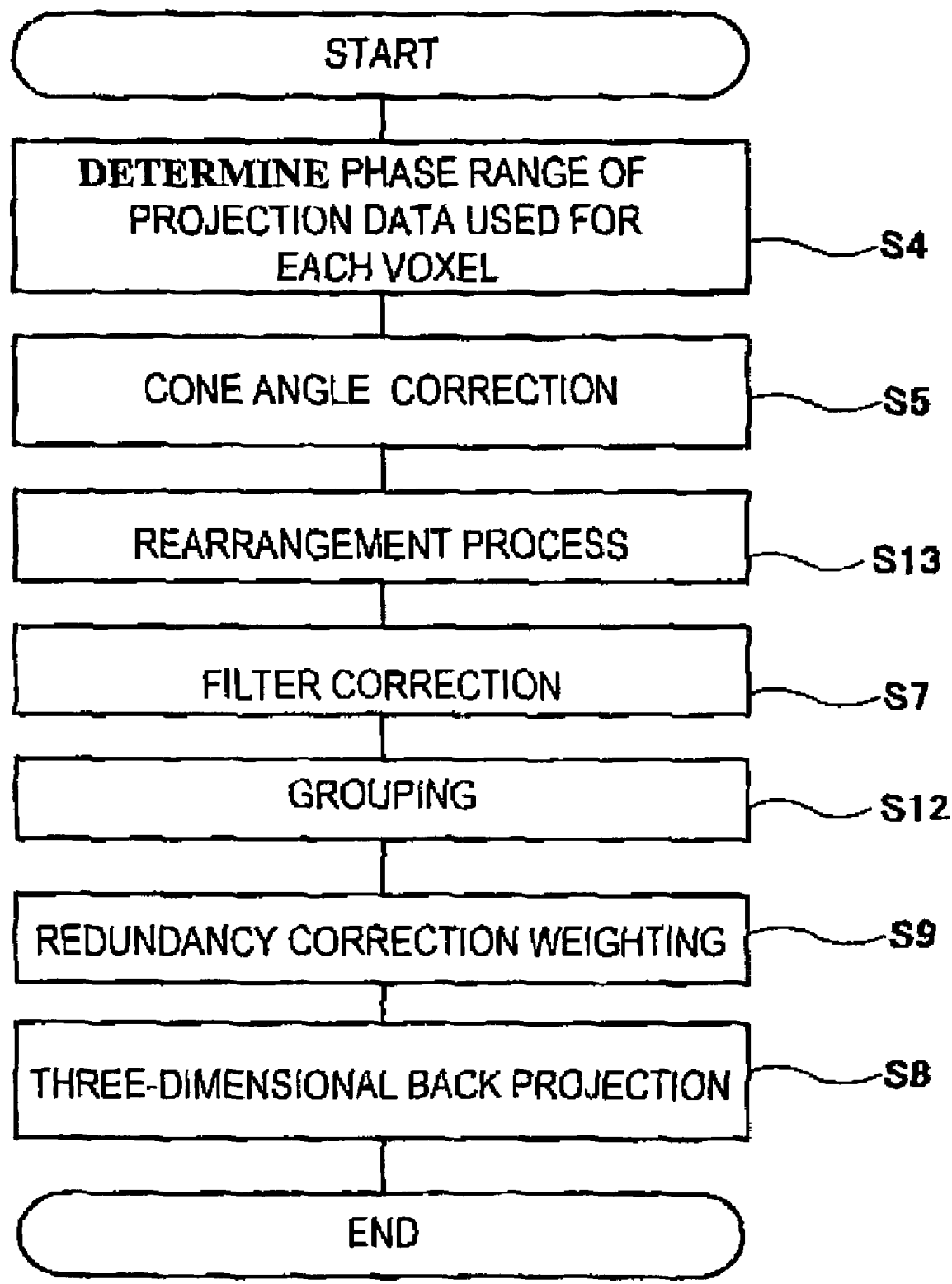
FIG. 24 is a flow chart showing a processing operation of another embodiment of the reconfiguration means of the present invention.

Thus, in order to enhance the speed of back projection which takes a maximum calculation time in creating an image, an image is taken with a view of a multiple of 4 and a fan beam is reconfigured in FIG. 23, and data is converted to data whose number of views is a multiple of 4 through the rearrangement process in step S13 and a parallel beam is reconfigured in FIG. 24, taking advantage of the fact that the reconfigured image array is square and images are taken while the detector is going around the reconfigured image.

In both cases, projection data whose phase in the go-around direction differs by $N\pi/2$ (N=1, 2, 3, ... ) [rad] is grouped and back projection is performed on the square image group by group, and therefore it is possible to reduce, for example, the number of calculations of the channel direction position in a full reconfiguration and interpolation coefficient to ¼ (it is possible to reduce the number of calculations to ½ in a half reconfiguration). This is because if the reconfigured image is square, data whose phase differs by $N\pi/2$ (N=1, 2, 3, ... ) [rad] and the square which is the reconfigured image have the same positional relationship.

Furthermore, the number of views is set to a multiple of 4 is to accurately calculate data whose phase differs by $N\pi/2$ (N=1, 2, 3, ... ) [rad]. Furthermore, in both cases of full reconfiguration and half reconfiguration, it is possible to create images by calculating the channel position within a range of ¼ ($\pi/2$[rad]) of one revolution. In terms of a full reconfiguration, the amount of calculation becomes ¼ and though the calculation is performed using only one calculator, it is possible to obtain a result close to the case where parallel calculations are performed using four calculators. That is, it is possible to realize high performance at a low cost. Needless to say, it is also possible to set the number of views to a multiple of 4 during image taking and perform reconfiguration directly from a fan beam without any rearrangement process (rebinning). Furthermore, when a display pixel is a hexagon, it is possible to group projection data whose phase in the go-around direction differs by $N\pi/3$ [rad] (N=1, 2, 3, ... ) and back project to the hexagonal image group by group. When the display pixel is polygonal and has C sides, the above described phase in the go-around direction is $2\pi/C$ [rad].

Next, group-by-group back projection will be explained.

Figure 25:
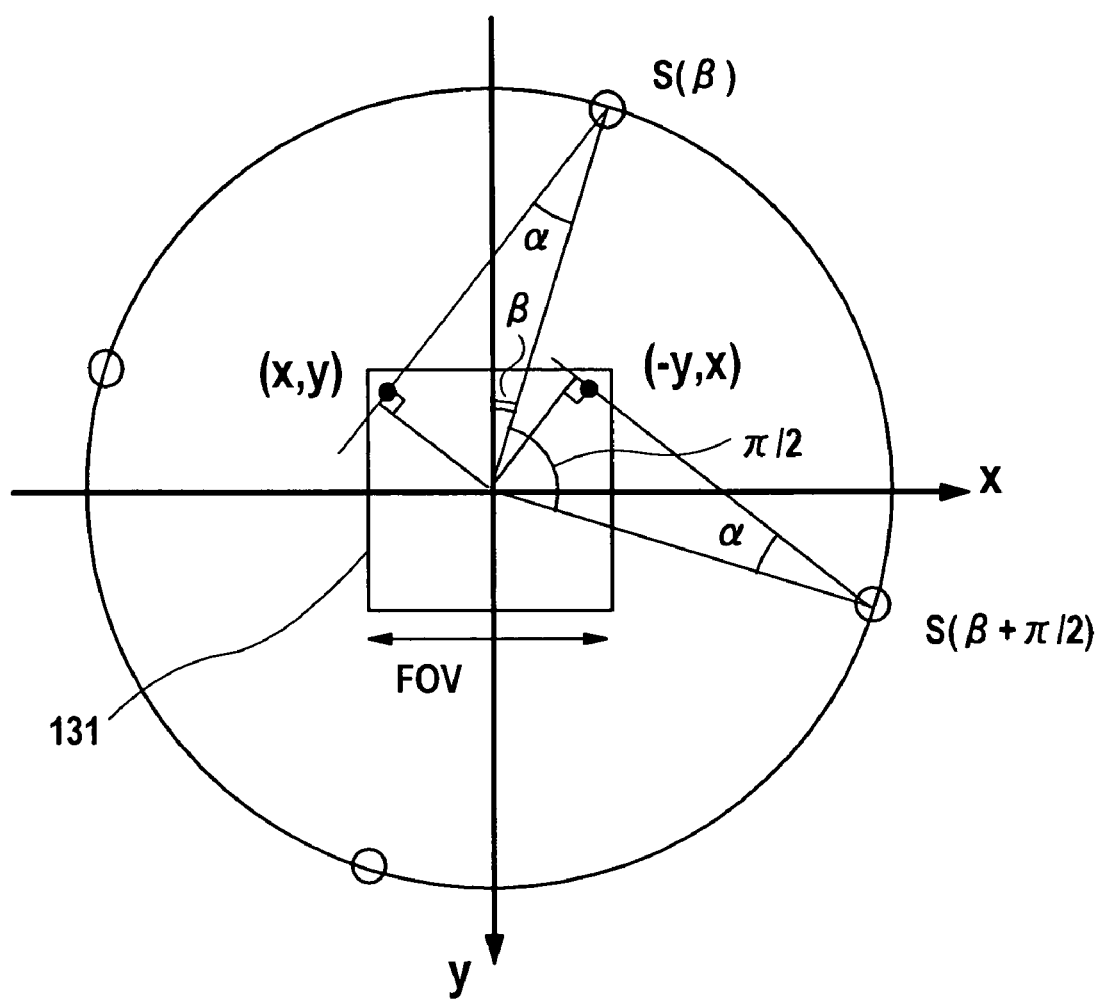
FIG. 25 illustrates back projection in group units in the grouping processing shown in FIG. 23.

First, as shown in FIG. 25, when only the X-Y plane is considered and a beam passing through a voxel (x, y) irradiated from a focus position $S(\beta)$ having phase $\beta$ is irradiated to a position u on the detector, group-by-group back projection processing is expressed by Expression 29 to Expression 32.

FIG. 25 shows a case where the amount of calculation in the channel direction is ¼ (view=4N; N is an integer) and the calculation start position is not limited. Furthermore, reference numeral 131 denotes a reconfiguration region.

$$I(x, y) = \frac{1}{\pi} \int_{Bs(x,y)}^{Bs(x,y)+\frac{\pi}{2}} fP_{para}(\phi, t, v) d\phi \qquad \text{[Expression 29]}$$

$$I(y, -x) = \frac{1}{\pi} \int_{Bs(x,y)}^{Bs(x,y)+\frac{\pi}{2}} fP_{para}\left(\phi + \frac{3\pi}{2}, t, v\right) d\phi \qquad \text{[Expression 30]}$$

$$I(-x, -y) = \frac{1}{\pi} \int_{Bs(x,y)}^{Bs(x,y)+\frac{\pi}{2}} fP_{para}(\phi + \pi, t, v) d\phi \qquad \text{[Expression 31]}$$

$$I(-y, x) = \frac{1}{\pi} \int_{Bs(x,y)}^{Bs(x,y)+\frac{\pi}{2}} fP_{para}\left(\phi + \frac{\pi}{2}, t, v\right) d\phi \qquad \text{[Expression 32]}$$

A beam irradiated from phase $\beta+\pi/2$ and passing through a voxel (−y, x) is irradiated to the position u on the radiation detector as in the case of being irradiated from phase $\beta$ to a voxel (x, y). Likewise, a beam irradiated from phase $\beta+\pi$ passes through a voxel (−x, −y) and is irradiated to the position u on the radiation detector. Likewise, a beam irradiated from phase $\beta+3\pi/2$ passes through a voxel (y, −x) and irradiated to the position u on the radiation detector. Thus, by performing back projection from the grouped data to four pixels which use the same radiation detector position data, it is possible to calculate the radiation detector position and reduce the number of times interpolation parameters are calculated.

Figure 26:
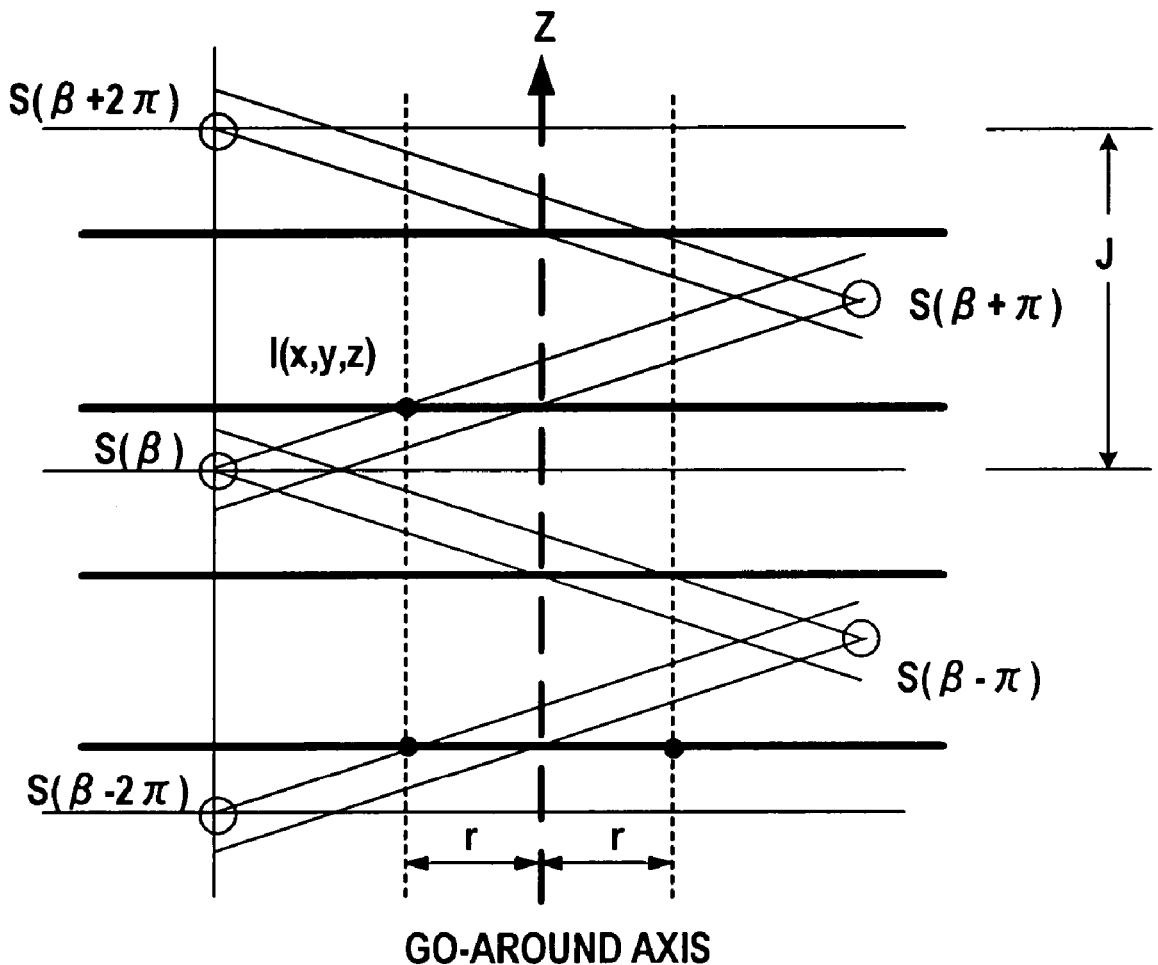
FIG. 26 illustrates another back projection in group units in the grouping processing shown in FIG. 23.

FIG. 26 shows a case where the amount of calculation in the row direction is ½n (where n denotes the number of data revolutions) and rpitch=J/2N (where N is an integer). As shown here, suppose an x-y-z space (Euclidean space) is considered and a relative moving speed between an object and radiation source in the go-around axis direction (e.g., bed feeding speed) is J and a beam passing through a voxel I (x, y, z) irradiated from a focus position $S(\beta)$ which is phase $\beta$ is irradiated to the position v in the go-around axis direction on the radiation detector. A beam irradiated from phase $\beta+2\pi$ and passing through a voxel (x, y, z+J) is irradiated to the position v in the go-around axis direction on the radiation detector as in the case where the beam is irradiated from phase β to the voxel I (x, y, z). Likewise, a beam irradiated from phase β+π passes through a voxel I (−X, −y, z+J/2) and is irradiated to the position v in the go-around axis direction on the radiation detector. Taking advantage of this, the object is associated with the relative moving speed of the radiation source in the go-around axis direction according to the reconfiguration intervals and data pieces with phases differing by Nπ (N=1, 2, 3 . . . ) [rad] from one another are grouped and back projected group by group.

According to such group-by-group back projection, by associating the pixel intervals of the voxel in the body axis direction at MDCT with the object and the relative moving speed of the radiation source in the go-around axis direction, it is possible to calculate the position in the body axis direction at high speed, and when an image is created from data of a plurality of revolutions obtained by taking images through a spiral scan, it is possible to enhance the speed of back projection which takes a maximum time to create images.

Here, the spiral period in the body axis direction is synchronized with the period of the reconfigured voxel in the body axis direction, and when, for example, the pixel interval (voxel pitch) in the body axis direction is rpitch[mm/(unit time)], the relative moving speed (bed moving speed) of the radiation source in the body axis direction with respect to the examinee is set to tables=2·N·rpitch (N=1, 2, 3, . . . ). In this way, at the phase of the radiation source which is Nπ (N=1, 2, 3, . . . ) [rad], the positions on the radiation detector at which the beams passing through the voxel I (x, y, z) whose body axis direction position is Z [mm] and the voxel I (−x, −y, N·J/2+Z) whose body axis direction position is (N·J/2)+Z [mm] intersect with each other are the same, and therefore calculating a beam passing through a voxel with a view at the time of back projection is equivalent to simultaneously calculating the row positions at phases differing by Nπ (N=1, 2, 3, . . . ) [rad] from each other. Thus, calculations of the row direction positions of the radiation detector and interpolation coefficients over the total measuring range are completed within the π [rad] range in the view direction.

In the above described embodiment, no rearrangement in the radiation detector row direction is performed so that descriptions in the rearrangement processing do not become complicated, but to enhance the speed of back projection, it is also possible to perform rearrangement in the row direction on the plane located at the rotation center which crosses the parallel beam at right angles as expressed in $P_{para}(\beta, t, v) = P_{fan}(\phi+\alpha, \alpha, (SID/SOD \cdot \cos(\alpha)) \cdot (v-J \cdot \alpha/2\pi))$ where α=arcsin(t/SOD) as shown in FIG. 13A so that points of intersection in the parallel beam channel direction become the same v coordinates. When such a rearrangement in the row direction is performed, it is possible to reduce the number of arcsin calculations used to calculate α at the time of back projection and realize faster processing. In this case, the operating data phase range for each voxel can be likewise calculated with H(x, y, φ) in the above described expression changed to Expression 33.

$$H(x, y, \phi) = \left(z - \frac{J \cdot \phi}{2\pi}\right) \cdot \frac{s\_tz\_dist(x, y, \phi)}{s\_tz\_dist(x, y, \phi) + w(x, y, \phi)}$$ [Expression 33]

Furthermore, in this case, v in Expression 22 is changed to v=(z−(J/2π) (φ+α))·SOD cos α/(SOD cos α−x sin φ+y cos φ) to obtain the projection beam used for back projection.

Furthermore, the tomograph in the above described embodiment is also applicable to products using X-rays, gamma rays, neutron rays, positron, electromagnetic energy or light. Furthermore, the scan system is not limited to any of first-generation to fourth-generation systems and this tomograph can also be used for a multi-tube CT incorporating a plurality of radiation sources and doughnut type tube CT. Furthermore, with regard to the shape of the radiation detector, this tomograph is also applicable to any radiation detector such as detectors arranged on a cylindrical surface centered on the radiation source, plane detectors, detectors arranged on a spherical surface centered on the radiation source and detectors arranged on a cylindrical surface centered on a go-around axis, etc. Furthermore, the position of a radiation detector corresponding to the reconfigured voxel is calculated every time, but for grouping in the channel direction, it is also possible to store a table of reconfiguration parameters calculated beforehand corresponding to N/4 revolutions (0≦β<Nπ/2, N=1, 2, 3 . . . ) in a memory, read this stored parameter table at the time of reconfiguration and realize reconfiguration based on this parameter table. Adopting such a configuration allows calculations of addresses corresponding to 4 views all at once. Such simplification of calculations is a technique unparalleled in conventional examples. The above described N/4 revolutions apply to the case where the shape of a display pixel is rectangular and when the display pixel is hexagonal, data can also be grouped every N/6 revolutions.

Embodiment 4

Figure 27:
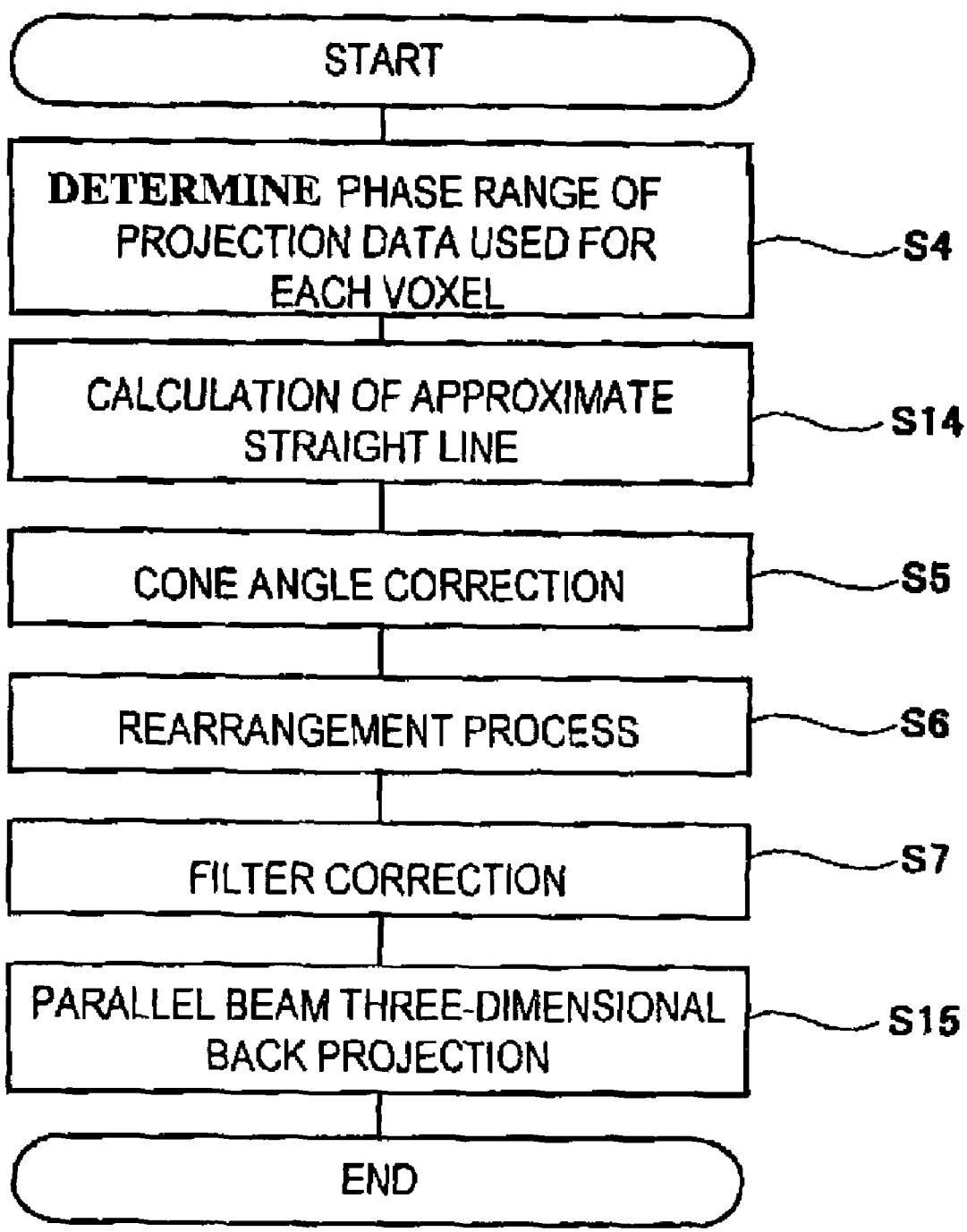
FIG. 27 is a flow chart showing a processing operation of a further embodiment of the reconfiguration means of the present invention.

FIG. 27 is a flow chart showing a processing operation of reconfiguration means 22 in a tomograph according to an embodiment of the present invention.

First, the reconfiguration means 22 is provided with operating data phase range calculation means for determining a projection data phase range capable of back projection for each reconfigured voxel, approximate straight line calculation means for calculating an approximate straight line for a curve indicating the radiation source position with respect to the channel direction position corresponding to a region in concern of parallel beam projection data obtained by a parallel beam of a parallel shape viewed from the go-around axis direction generated from the radiation source, cone angle correction means for multiplying each row of projection data by a coefficient which is dependent on the angle of inclination of radiation from the radiation source, one-dimensional rearrangement processing means for obtaining parallel beam projection data from the fan beam projection data obtained by a fan-shaped fan beam viewed from the go-around axis direction generated from the radiation source, filter correction means for superimposing a reconfiguration filter on the parallel beam projection data and creating filter-processed parallel beam projection data and parallel beam three-dimensional back projection means for three-dimension back projecting the filter-processed parallel beam projection data to a back projection region corresponding to a region in concern along the approximate irradiation trace of the radiation beam calculated using the approximate straight line based on the determined projection data range capable of back projection.

Based on the above described structure, the data range used for each voxel is determined using the operating data phase range calculation means in step S4 first, and an approximate straight line for a curve indicating the radiation source position with respect to the channel direction position of the parallel beam projection data obtained by a parallel beam of a parallel shape viewed from the go-around axis direction generated from the radiation source by the approximate straight line calculation means is calculated in step S14. Next, in step S5, the cone angle correction means multiplies each row of the projection data by a coefficient which is dependent on the angle of inclination of radiation and in step S6, the one-dimensional rearrangement processing means associates the fan beam projection data obtained from a fan-shaped fan beam viewed from the go-around axis direction generated from the radiation source with the parallel beam projection data. Then, in step S7, the filter correction means superimposes a reconfiguration filter on the parallel beam projection data and creates parallel beam projection data subjected to filter processing. Then, in step 15, based on the projection data range capable of back projection determined by the parallel beam three-dimensional back projection means, the parallel beam projection data subjected to filter processing is three-dimensional back projected to the back projection region corresponding to the region in concern along the approximate irradiation trace of the radiation beam calculated using an approximate straight line.

Steps S4 to S7 are the same as those already explained in other embodiments.

The calculation of an approximate straight line by the approximate straight line calculation means in step S14 for the curve indicating the radiation source position with respect to the channel direction position of the parallel beam projection data obtained by a parallel beam of a parallel shape viewed from the go-around axis direction generated from the radiation source will be explained.

Here, a technique using a least squares method will be shown. First, when an approximated curve and an approximate curve will be considered. A coordinate $Z_i$ of the focus at the channel i position of a parallel beam is expressed by the following Expression 34 and an approximate straight line $z_A$ except an arcsin calculation is expressed by the following Expression 35. Here, suppose the position of the channel i of the parallel beam in the t axis direction is $t_i$.

$$z_i = J \cdot \arcsin(t_i / SOD)/2/\pi \qquad \text{[Expression 34]}$$

$$z_A(t_i) = A \cdot t_i + B \qquad \text{[Expression 35]}$$

A, B in the expression can be calculated more specifically as follows.

When points on the approximated curve within a diameter FOV of the circular region in concern shown in FIGS. 28A and 28B are approximated with an approximate straight line and an evaluation function for minimizing the error between the approximated curve and approximate straight line is used according to a least squares method, the points can be expressed by Expression 36. $N_t$ denotes the number of samples.

$$E^2(A, B) = \sum_{i=1}^{N_t} (z_i - z_A(t_i))^2 = \sum_{i=1}^{N_t} (z_i - A \cdot t_i - B)^2 \qquad \text{[Expression 36]}$$

Here, Expression 36 is minimized to determine A, B. With the minimum values, the differentiation values with respect to A and B of Expression 44 are zeros as shown in Expression 37 and Expression 38.

$$O = \frac{\partial E^2}{\partial B} = -2 \sum_{i=1}^{N_t} (z_i - A \cdot t_i - B) \qquad \text{[Expression 37]}$$

$$O = \frac{\partial E^2}{\partial A} = -2 \sum_{i=1}^{N_t} \{t_i \cdot (z_i - A \cdot t_i - B)\} \qquad \text{[Expression 38]}$$

For simplicity, when the following sums in Expression 39 are introduced and these sums are substituted into Expression 36 and Expression 37, then Expression 40 and Expression 41 are obtained.

$$S \equiv \sum_{i=1}^{N_t} 1, \quad S_t \equiv \sum_{i=1}^{N_t} t_i, \quad S_z \equiv \sum_{i=1}^{N_t} z_i, \quad S_{tt} \equiv \sum_{i=1}^{N_t} t_i^2, \qquad \text{[Expression 39]}$$

$$S_{tz} \equiv \sum_{i=1}^{N_t} (t_i \cdot z_i)$$

$$B \cdot S_t + A \cdot S_t = S_z \qquad \text{[Expression 40]}$$

$$B \cdot S_t + A \cdot S_{t \cdot t} = S_{tz} \qquad \text{[Expression 41]}$$

The solution of these simultaneous equations is given in the following Expression 42 to Expression 44.

$$\Delta \equiv S \cdot S_{tt} - (S_t)^2 \qquad \text{[Expression 42]}$$

$$A = (S_{tt} \cdot S_z - S_t \cdot S_{tz})/\Delta \qquad \text{[Expression 43]}$$

$$B = (S \cdot S_{tz} - S_t \cdot S_z)/\Delta \qquad \text{[Expression 44]}$$

Thus, by substituting this into $z_A(t_i) = A \cdot t_i + B$ shown in Expression 35, it is possible to obtain Expression 45.

$$z_A(t_i) = ((S_{tt} \cdot S_z - S_t \cdot S_{tz})/\Delta) \cdot t_i + (S \cdot S_{tz} - S_t \cdot S_z)/\Delta \qquad \text{[Expression 45]}$$

Next, based on the determined projection data range capable of back projection in step S15 shown in FIG. 27, the parallel beam three-dimensional back projection means which performs three-dimensional back projection on the parallel beam projection data subjected to filter processing to the back projection region corresponding to the region in concern along the approximate irradiation trace of the radiation beam calculated using an approximate straight line will be explained.

As shown in FIG. 28A and FIG. 29, suppose the reconfigured voxel is I (x, y, z), the relative movement distance of the radiation source 11 with respect to the examinee per rotation of the scanner on the radiation detector is J, the go-around axis direction position on the cylindrical radiation detector 13 centered on the radiation source 11 is v, the position on the T axis substantially perpendicular thereto is t and the coordinates are T(x, y, φ), then Expression 46 to Expression 50 are obtained respectively. In FIG. 29, reference character A denotes an image array of I(x, y, z) and 111 denotes an X-ray beam.

Expression 46 shows a weighting three-dimensional back projection along the beam trace over the back projection data range determined by the data phase range calculation means.

Expression 50 shows a radiation beam trace calculated using an approximate straight line.

$$I(x, y, z) = \int_{B_s(x,y,z)}^{B_e(x,y,z)} fP_{para}(\phi, t, v) \cdot W\left(\phi - B_s(x, y, z) - \frac{f\pi}{2}\right) \cdot d\phi \qquad \text{[Expression 46]}$$

$$L(x,y,\phi) = \sqrt{SOD^2 - t^2} - x\cdot\sin\phi - y\cdot\cos\phi \quad \text{[Expression 47]}$$

$$t(x,y,\phi) = x\cdot\cos\phi + y\cdot\sin\phi \quad \text{[Expression 48]}$$

$$v = (z_f - z_S)\cdot SID/L(\phi,x,y) \quad \text{[Expression 49]}$$

$$z_S = \frac{J\cdot\left(\phi + \arcsin\left(\frac{t}{SOD}\right)\right)}{2\pi} + z_{SO} \quad \text{[Expression 50]}$$

$$\cong \frac{J\cdot\phi}{2\pi} + A\cdot t + B + z_{SO}$$

Here, in the three-dimensional back projection, projection data and a reconfigured image which should actually be handled discretely are handled as continuous data, and therefore it is actually necessary to calculate the data discretely using a combination of interpolation in three directions of the phase direction (time direction), radiation detector row direction and radiation detector channel direction using a publicly known interpolation method such as Lagrange interpolation.

As is evident from the above described reconfiguration method, Expression 50 has a large calculation load with an arcsin calculation included in the calculation of the focus z position of the conventional parallel beam as seen from a comparison with Expression 1, but this arcsin calculation is replaced by an approximate straight line, and therefore it is possible to simplify an amount of calculation of the parallel beam three-dimensional back projection method and drastically enhance the processing speed.

However, this reconfiguration method may involve the risk of deterioration of accuracy due to the use of the approximate straight line, but this error remains at such a level that even when the diameter of FOV of a circular region in concern is 410 [mm], the distance SOD between the focus and go-around axis is 600 [mm], the distance SID between the focus and detector is 1000 [mm], the number of detector rows row is 64 [rows], the detector element direction size dapp is 1 [mm] and the relative moving speed T is 60 [mm/rot], a maximum error is on the order of 0.023 [mm] and absolute error average is on the order of 0.014 [mm]. This error is an error on the order of 2% (maximum 4%) considering the measuring accuracy and the z direction width of the beam at the rotation center of 0.6 [mm] and is at a totally insignificant level taking into consideration that noise is included in measuring data. That is, the approximate calculation will not lead to deterioration of image quality.

Furthermore, in the process of determining the phase range for each voxel shown in step S4, a phase range of $f\pi$ [rad] is determined in the view direction and a three-dimensional reconfiguration method whereby redundancy correction is performed using a weighting function is used, and therefore by providing the data with redundancy (extending the back projection phase width beyond 180 degrees) and assigning weights using a weighting function, it is possible to reduce discontinuity at the data ends, that is, at the of start and end of image taking and obtain an image with the influence of movement of the examinee suppressed to a minimum.

Furthermore, when a fan beam is rearranged to parallel beams and then one-slice reconfigured image is reconfigured through three-dimensional back projection, the conventional art uses the same back projection phase range for all voxels, and the z direction positions of the focuses of parallel beams are not the same in the channel direction, and therefore a maximum cone angle back projected at each voxel increases. That the maximum cone angle used increases means that a wider detector is required depending on the go-around axis z direction, that is, the relative moving speed in the z direction between the examinee and focus decreases and the measuring throughput deteriorates. However, in this embodiment, the maximum cone angle of the beam used for back projection is reduced as described above, and therefore it is possible to reconfigure a detector which is narrow in the z direction and improve the measuring throughput.

Embodiment 5

Figure 30:
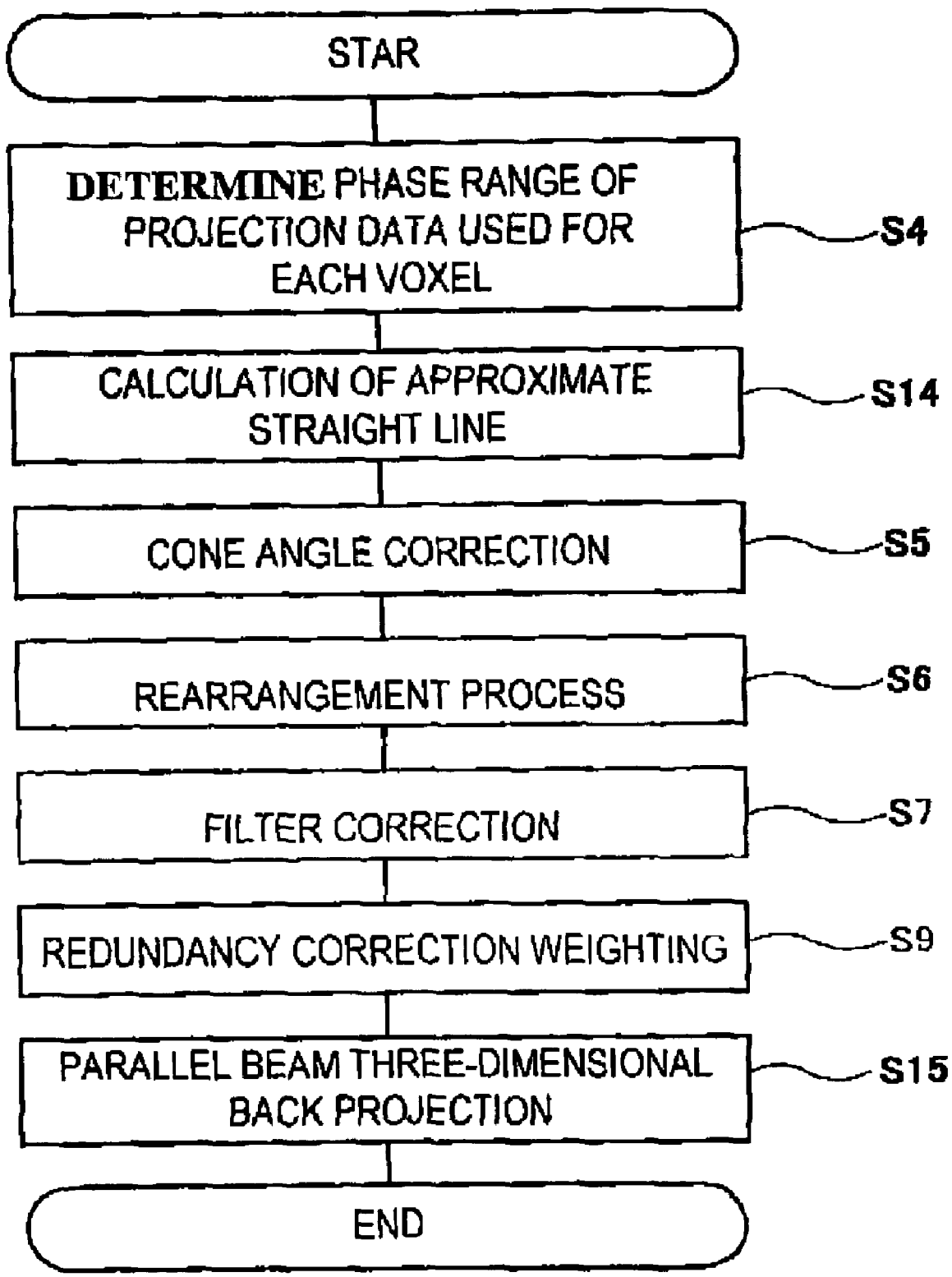
FIG. 30 is a flow chart showing a processing operation of a still further embodiment of the reconfiguration means of the present invention.

FIG. 30 is a flow chart showing a processing operation of reconfiguration means 22 of a tomograph according to a still further embodiment of the present invention.

Here, the reconfiguration means 22 consists of operating data phase range calculation means for determining projection data phase range capable of back projection for each reconfigured voxel, approximate straight line calculation means for calculating an approximate straight line for a curve indicating the radiation source position with respect to the channel direction position of parallel beam projection data obtained by a parallel beam of a parallel shape viewed from the go-around axis direction generated from a radiation source, cone angle correction means for multiplying each row of projection data by a coefficient which is dependent on the angle of inclination of radiation, one-dimensional rearrangement processing means for associating fan beam projection data obtained from a fan beam of a fan shape viewed from the go-around axis direction generated from the radiation source with the parallel beam projection data, filter correction means for superimposing a reconfiguration filter on the corrected projection data and creating filter-processed projection data, redundancy correction weighting means for carrying out a redundancy correction on the filter-processed projection data over a projection data range $f\pi$ determined by the operating data phase range calculation means using a weighting function whose shape changes according to the phase width and parallel beam three-dimensional back projection means for performing three-dimensional back projection to a back projection region along an approximate irradiation trace of the radiation beam calculated based on the approximate straight line obtained by the approximate straight line calculation means while carrying out weighting processing on the filter-processed projection data using this redundancy correction weighting means.

As in the case of FIG. 27, such reconfiguration means 22 superimposes a reconfiguration filter on the parallel beam projection data using the filter correction means in step S7, generates filter-processed parallel beam projection data and then in step S9, carries out a redundancy correction on the filter-processed projection data created by the filter correction means using a weighting function by the redundancy correction weighting means over the data range $f\pi$ determined by the operating data phase range calculation means. Then, while performing weighting processing using this redundancy correction weighting means, in step 15, the filter-processed parallel beam projection data is three-dimension back projected to a back projection region corresponding to a region in concern along an approximate irradiation trace of the radiation beam calculated using an approximate straight line based on the projection data range capable of back projection determined by the parallel beam three-dimensional back projection means.

Details of each step have already been explained with the same step numbers assigned, and therefore explanations thereof will be omitted.

The embodiment explained using the above described flow chart in FIG. 27 has described the calculation of a data range whose maximum cone angle is narrow in the determining process of the operating data phase range by the operating data phase range determining means, but it is also possible to determine a data range for each voxel so that in step S4, the difference in the cone angle (corresponding to the absolute value of v) at the ends (data start/end positions) of the back projection data range becomes a minimum and perform a similar reconfiguration process based on this determined data range.

An example of the method of determining the operating data phase range for each voxel (calculation of a data range whose back projection phase width is narrow) will be explained. First, the case where the z direction size ($Z_{det}$) of the radiation detector is sufficiently wide will be shown. When data can be acquired in the same go-around phase range at all reconfigured voxels at the same z position (when reconfiguration is possible), or more specifically, when the image taking condition in Expression 51 is satisfied, the phase range having a small difference in the back projection phase range with respect to a voxel whose z position is located within the same plane is expressed by Expression 52, where θ0 is the phase at which the z position of the focus corresponds to the voxel position, dapp is the z direction size of the detector element and row is the number of detector rows.

$$J \leq \frac{dapp \cdot (row-1) \cdot (SOD - FOV/2)}{\frac{SID}{2\pi}\left(f\pi + 2\arcsin\left(\frac{FOV}{2SOD}\right)\right)}$$ [Expression 51]

$$\theta_0 - f\pi/2 \leq \theta < \theta_0 + f\pi/2$$ [Expression 52]

However, when the relative moving speed between the examinee and the focus is high and it is impossible to acquire data at all voxels within the same phase range, that is, when the above described image taking condition is not satisfied, it is not possible to select the phase range as expressed in Expression 52. In such as case, it is possible to determine the phase range using the method shown below.

If the distance between the radiation source and the rotation center is SOD, the relative movement distance of the radiation source relative to the examinee per rotation of the scanner on the radiation detector is J, the go-around phase of the fan beam source is β, the beam spreading angle between the beam directed to the reconfigured voxel and central beam is α and the go-around phase of the parallel beam is φ, then the radiation source position $S(\beta)=S(x_s, y_s, z_s)$ is expressed by Expression 2 described above.

In terms of parallel beams obtained through a rearrangement process, this is expressed by Expression 12 described above.

Here, if the traveling direction of the parallel beam is w and the direction perpendicular to this w is t, then the t coordinate and w coordinate when the parallel beam with phase φ passes through the coordinates (x, y) are expressed by Expression 13 and Expression 14 described above and the distance between the radiation source and tz plane (plane passing through the go-around axis and perpendicular to the parallel beam) is expressed by Expression 6 described above. Furthermore, when the parallel beam with phase φ passes through the reconfigured voxel (x, y, z) and crosses the detector whose distance from the radiation source is SID and the coordinates of the detector in the v axis (go-around axis) direction are H(x, y, φ), then this can be expressed by Expression 7 described above.

Furthermore, if a phase range index is f, in order to back project the reconfigured voxel I (x, y, z) within a phase range having a small difference in the back projection phase range with respect to the voxel whose z position is located within the same plane, the z direction position of the radiation detector when the beams irradiated from the end positions $B_s$ and $B_e$ of the phase range fπ used pass through the reconfigured voxel and cross the radiation detector must be located within the range of the detector, and therefore if the go-around phase when the z direction position of the focus is at the position of the reconfigured voxel is $\theta_0$, it is possible to select such φ that satisfies Expression 53 and Expression 54 and approximates to $\theta_0-f\pi/2$ infinitely.

$$H(x,y,\phi) \leq dapp \cdot (row-1)/2$$ [Expression 53]

$$H(x,y,f+f\pi) \geq -dapp \cdot (row-1)/2$$ [Expression 54]

Figure 31:
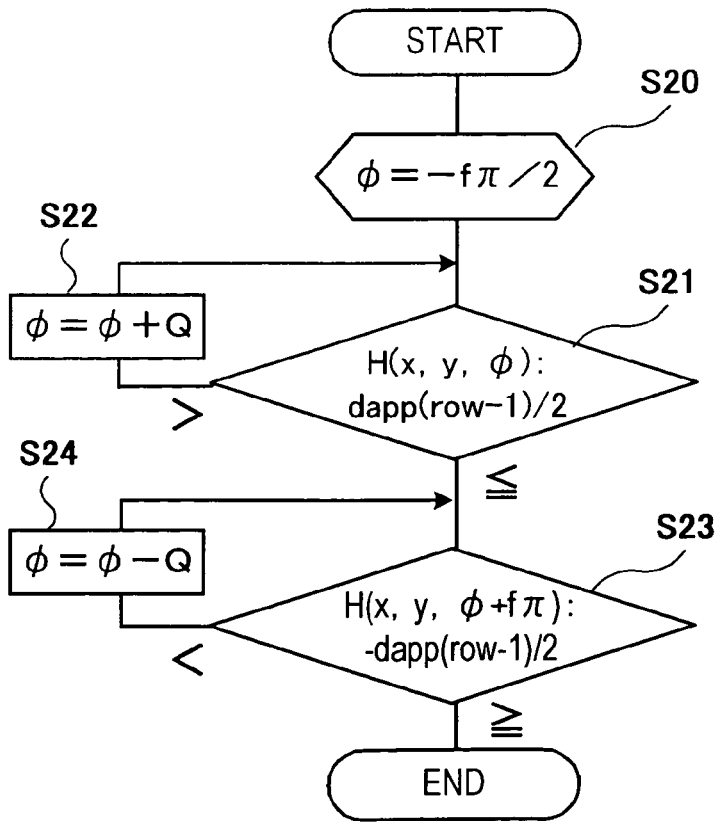
FIG. 31 is a flow chart showing an operation of phase range calculation processing on the data used in FIG. 30.

More specifically, when $\theta_0=0$, as in step S20 shown in FIG. 31, if the initial value of φ is $-f\pi/2$ and the phase accuracy to be calculated is Q (e.g., Q is a phase angle by which the focus advances per one view), if φ is small (φ<0), H (x, y, φ) decreases as φ increases and H(x, y, φ) increases as φ decreases, and therefore if images are taken under reconfigurable conditions, the processes shown in Expression 55 and Expression 56 are repeated until Expression 61 and Expression 62 are satisfied respectively as shown in steps S21 to S24. This makes it possible to satisfy Expression 57 and Expression 58 and select φ so as to approximate to $\theta_0-f\pi/2$ as much as possible. In this way, the phase range (Bs≦φ<Be) becomes the same as that expressed by Expression 12 and Expression 13.

if $[dapp \cdot (row-1)/2 - H(x,y,\phi)<0], \phi=\phi+Q$ [Expression 55]

if $[dapp(row-1)/2 + H(x,y,\phi f\pi)<0], \phi=\phi-Q$ [Expression 56]

$H(x,y,\phi) \leq dapp \cdot (row-1)/2$ [Expression 57]

$H(x,y,f\pi) \geq -dapp \cdot (row-1)/2$ [Expression 58]

In this phase range calculation process, by determining the back projection phase range for each voxel so that the number of views is reduced, it is possible to improve time resolution for each voxel and obtain good image quality in regions where the examinee moves drastically by combining this with the aforementioned weighting back projection. Furthermore, by setting the back projection phase range for each voxel to within a time range in which images are taken at the same time wherever possible so that the time positions of the respective voxels in the displayed images come closer to one another, it is possible to shorten the time width contributing to the reconfigured image and improve time resolution. The back projection phase range in this case is ideally the same back projection phase range at all voxels, but even when the relative moving speed between the examinee and focus is high and it is impossible to obtain data at all voxels within the same phase range, it is possible to determine the back projection phase range for each voxel so that the examinee and focus come as close as possible to each other.

To arbitrarily make changeable the relationship between a noise level and body axis resolution in the reconfigured image, a body axis (go-around axis) direction filter whose spatial frequency characteristic is changeable in the row direction is preferably superimposed on the projection data. This superimposition of the body axis direction filter (body axis direction filtering) may be performed before or after the one-dimensional rearrangement process. The superimposition may also be included in the filter correction processing. Furthermore, the above described embodiment uses a tomograph using X-rays, but the present invention is not limited to such a tomograph and is also applicable to a tomograph using neutron rays, positron, gamma rays or light. Furthermore, the scan system is not limited to any one of the first-generation, second-generation, third-generation or fourth-generation systems, but can also be used for a multi-tube CT provided with a plurality of radiation sources, cathode scan CT or electron beam CT. Furthermore, the shape of the radiation detector is also applicable to any one of radiation detectors such as radiation detectors arranged on a cylindrical surface centered on a radiation source, plane detectors, radiation detectors arranged on a spherical surface centered on the radiation source, radiation detectors arranged on a cylindrical surface centered on the go-around axis, etc. Furthermore, the tomograph is not limited to a spiral orbit scan, but is also applicable to a circular orbit scan. Furthermore, projection data and reconfigured image that should actually be handled discretely are handled as continuous data, and therefore it is desirable to calculate discretely through interpolation in three directions of phase direction, row direction and channel direction of the radiation detector using an interpolation method such as Lagrange interpolation. Furthermore, the above described embodiment approximates arcsin with one approximate straight line, but it is also possible to approximate arcsin using a plurality of approximate straight lines (using different approximate straight lines according to the distance from the go-around axis). Furthermore, a nonlinear function value of the present invention can also be calculated using advance calculations (tabulation) and interpolation for speed enhancement.

In the above described embodiments, the process (S4) of determining the phase range of the projection data used for each voxel in FIG. 9 is also applicable to other embodiments of the reconfiguration means 22.

The redundancy correction weighting process (S9) in FIG. 16 is also applicable to other embodiments of the reconfiguration means 22.

The process (S11) of rearrangement into data with a view of a multiple of 4 and process (S12) of grouping in FIG. 23 are also applicable to other embodiments of the reconfiguration means 22.

The process (S13) of rearrangement in FIG. 24 is also applicable to other embodiments of the reconfiguration means 22.

The approximate straight line calculation process (S14) and parallel beam three-dimensional back projection process (S15) in FIG. 27 are also applicable to other embodiments of the reconfiguration means 22.

As described above, according to the tomograph of the present invention, when reconfiguration is performed from data obtained through a scan, it is possible to reduce the distortion due to data discontinuity to a minimum and obtain images of high quality without producing any streak artifact in the reconfigured image.

Furthermore, according to the tomograph of the present invention, it is possible to simplify an arcsin calculation used so far, enhance the speed drastically and obtain images of high quality in a short time by calculating an approximate straight line for a curve indicating the radiation source position with respect to the channel direction position of parallel beam projection data obtained by a parallel beam of a parallel shape viewed from the go-around axis direction generated from the radiation source.

All the foregoing descriptions have been presented about the embodiments, but it is obvious for those skilled in the art that the present invention is not limited to these embodiments but can be altered or modified in various ways without departing from the spirit and accompanying claims.

This application with claims of priority is based on Japanese Patent Application No. 2002-304463 and Japanese Patent Application No. 2003-078125, entire content of which is expressly incorporated by reference herein.

The invention claimed is:

1. An X-ray tomograph comprising:
 a radiation source and a radiation detector arranged opposite to each other, between which a bed with an examinee placed thereon is provided, said radiation source and radiation detector turning around said bed which is configured to move with respect to a go-around axis, radiation irradiated from said radiation source and passing through the examinee being detected using said radiation detector and being converted to projection data; and
 reconfiguration means for creating a three-dimensional tomographic image in a region in concern of the examinee from the projection data,
 wherein said reconfiguration means determines, for each voxel, a projection data phase range as an angle between 180 and 360 degrees from projection data obtained at a spiral orbit scan so that a difference in absolute values of cone angles at both ends of the projection data phase range used is minimized, superimposes a reconfiguration filter, assigns weights to data of a same phase or opposite phase for each phase for the projection data phase range1 and three-dimension back projects the filter-processed projection data over said projection data phase range determined for each voxel along an irradiation trace of a radiation beam.

2. The X-ray tomograph according to claim 1, wherein the projection data phase range used is determined so as to be the same phase range for each voxel.

3. The X-ray tomograph according to any one of claims 1 and 2, wherein projection data for a number of images taken per rotation that is a multiple of a number of sides C of a rectangle or hexagon is acquired, and said reconfiguration means comprises back projection means for superimposing said reconfiguration filter on the acquired projection data, grouping data at a same channel position and having projection phases in a go-around direction shifting by $2N\pi/C$ (N=1, 2, 3, . . . ) radians at a time and performing back projection to a square image array group by group.

4. The X-ray tomograph according to any one of claims 1 and 2, wherein said reconfiguration means converts the projection data obtained to data including fan beam data and parallel beam data for a number of images taken per rotation that is a multiple of a number of sides C of a rectangle or hexagon, superimposes the reconfiguration filter on the converted data, groups data at a same channel position and having projection phases in a go-around direction shifting by $2N\pi/C$ (N=1, 2, 3, . . . ) radians at a time and performs back projection to a square image array group by group.

5. The X-ray tomograph according to claim 1, further comprising associating means for associating voxel pitch in a body axis direction with a relative moving speed between the examinee and said radiation source in a go-around axis direction.

6. The X-ray tomograph according to claim 5, wherein said associating means is constructed so that a relationship between voxel pitch rpitch in the body axis direction of a square image and the relative moving speed in the go-around axis direction of the examinee and said radiation source is expressed by 2·N·rpitch (N=1, 2, 3 . . . ).

7. The X-ray tomograph according to claim 6, wherein at the phase of Nπ (N=1, 2, 3, . . . ) radians of the radiation source, the position on the radiation detector at which the beam passing through a voxel I (x, y, Z) whose body axis direction position is Z millimeters intersects and the position on the radiation detector at which the beam passing through a voxel I (−x, −y, NJ/2+Z) whose body axis direction position is N·J/2+Z millimeters intersects are the same.

* * * * *